United States Patent [19]

Lattrell et al.

[11] Patent Number: 4,647,556

[45] Date of Patent: Mar. 3, 1987

[54] CEPHALOSPORIN DERIVATIVES

[75] Inventors: Rudolf Lattrell, Königstein; Reiner Kirrstetter; Wilfried Schwab, both of Kelkheim; Walter Dürckheimer, Hattersheim am Main; Gerhard Seibert, Darmstadt, all of Fed. Rep. of Germany

[73] Assignee: Hoechst Aktiengesellschaft, Fed. Rep. of Germany

[21] Appl. No.: 471,649

[22] Filed: Mar. 3, 1983

[30] Foreign Application Priority Data

Mar. 4, 1982 [DE] Fed. Rep. of Germany ....... 3207840

[51] Int. Cl.⁴ ................ C07D 501/38; A61K 31/545
[52] U.S. Cl. .................................. 514/206; 514/203; 540/225
[58] Field of Search ............. 544/25; 424/246; 514/203, 206

[56] References Cited

U.S. PATENT DOCUMENTS

| | | | |
|---|---|---|---|
| 4,237,168 | 12/1980 | Cimarusti et al. | 544/29 |
| 4,258,041 | 3/1981 | O'Callaghan et al. | 544/25 |
| 4,298,606 | 11/1981 | Ochiai et al. | 544/27 |
| 4,440,766 | 4/1984 | Kamiya et al. | 544/27 |
| 4,470,983 | 9/1984 | Blumbach et al. | 544/21 |
| 4,501,739 | 2/1985 | Lunn | 544/25 |

*Primary Examiner*—Nicholas S. Rizzo
*Attorney, Agent, or Firm*—Finnegan, Henderson, Farabow, Garrett & Dunner

[57] ABSTRACT

The invention relates to cephem derivatives of the general formula I

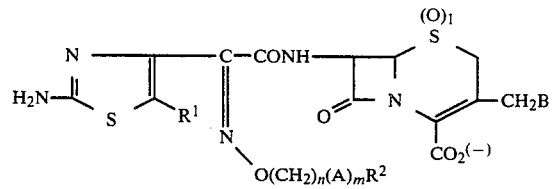

and their physiologically acceptable acid addition salts, to pharmaceutical formulations active against bacterial infections, to processes for preparing the compounds and formulations, and to the use of the compounds for combating bacterial infections.

3 Claims, No Drawings

CEPHALOSPORIN DERIVATIVES

The invention relates to new cephalosporin derivatives and a process for their preparation, in particular to polar cephem derivatives which are substituted in the 3-position of the cephem ring by certain pyridinium-methyl radicals and which have a very good antimicrobial action against Gram-positive and Gram-negative bacteria and which are therefore suitable for use as medicaments for treating microbial infections The invention therefore relates to cephem derivatives of the general formula I

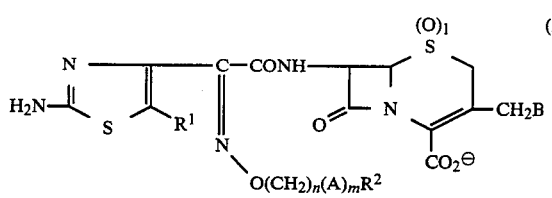

and to their physiologically acceptable acid addition salts in which $R^1$ denotes hydrogen or halogen, $R^2$ denotes a group $-CO_2R^3$ in which $R^3$ denotes hydrogen, $C_1-C_4$-alkyl, $-CH_2OC_1-C_4$-alkyl, $-CH_2OOC-C_1-C_4$-alkyl or one equivalent of an alkali metal, alkaline earth metal, ammonium or of an organic amine base, a nitrile group or a carbamoyl group $-CONH_2$ which can be monosubstituted or disubstituted on the nitrogen, l, m and n in each case denote 0 or 1, A denotes an aryl radical, a group

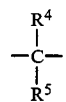

in which $R^4$ and $R^5$ can be identical or different and form hydrogen, aryl, a $C_1-C_4$-alkyl group or, together with the carbon to which they are bonded, a methylene or a $C_3-C_7$-cycloalkylidene group, and alkyl and cycloalkyl can be further monosubstituted or polysubstituted, B denotes a pyridinium radical

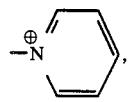

which can be monosubstituted or polysubstituted by identical or different substituents, namely by substituted $C_1-C_6$-alkyl, of which 2 alkyl groups can also be linked to form a possibly substituted di- to deca-methylene ring in which a C atom can be replaced by a heteroatom and which can additionally contain one or two double bonds, by cyano-$C_1-C_3$-alkyl, epoxy-$C_2-C_6$-alkyl, trifluoromethyl or pentafluoroethyl, by hydroxyiminomethyl or $C_1-C_4$-alkoxyiminomethyl, by optionally substituted $C_2-C_6$-alkenyl, by $C_2-C_6$-alkynyl, by $C_3-C_7$-cycloalkyl or $C_3-C_7$-cycloalkylmethyl, in which two substituents the ring can also be substituted and in which a C atom can be replaced by a heteroatom, by $C_4-C_7$-cycloalkenyl, by optionally subsisubstituted, by $C_4-C_7$-cycloalkenyl, by optionally substituted $C_1-C_6$-alkoxy, by epoxy-$C_2-C_6$-alkenyloxy or $C_2-C_6$-alkynyloxy, by halogen, cyano, hydroxyl or mercapto, by $C_1-C_6$-alkysulfonyl, $C_1-C_6$-alkylsulfinyl or $C_1-C_6$-alkylthio which is optionally substituted in the alkyl part, by methylsulfonyl, methylsulfinyl or methylthio which is substituted on the methyl radical, by $C_2-C_6$-alkenylthio, $C_2-C_6$-alkenylsulfinyl or $C_2-C_6$-alkenylsulfonyl, by optionally substituted phenyl, benzyl or heteroaryl, by formyl or ketalized formyl, by optionally substituted $C_1-C_6$-alkylcarbonyl which can also be present in ketalized form, by arylcarbonyl, by $C_1-C_6$-alkylcarbonylamino, by carboxyl or $C_1-C_6$-alkoxycarbonyl, by carbamoyl, which can be monosubstituted or disubstituted on the nitrogen, by optionally substituted carbazoyl, by sulfamoyl, which can be monosubstituted on the nitrogen, or by pyridyl or 4-pyridon-1-yl, and in which the group $-O-(CH_2)_n(A)_mR^2$ is in the syn position.

The present invention relates in particular to compounds in which $R^1$, $R^2$, A, l, n and m have the above-mentioned meanings and B denotes a pyridinium radical

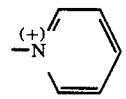

which can be 1-substituted or polysubstituted by identical or different substituents, namely by $C_1-C_6$-alkyl which can be monosubstituted or polysubstituted by hydroxyl, carboxyl, $C_1-C_6$-alkyloxycarbonyl, formyl or $C_1-C_6$-alkylcarbonyl, the carbonyl groups of which can also be present in ketalized form, carbamoyl, N-hydroxycarbamoyl, sulfo, $C_1-C_6$-alkyloxy, hydroxy-$C_1-C_6$-alkyloxy, $C_1-C_6$-alkylthio, $C_1-C_6$-alkylsulfinyl, $C_1-C_6$-alkylsulfonyl, $C_2-C_6$-alkenyloxy, $C_2-C_6$-alkenylthio, $C_2-C_6$-alkenylsulfinyl or $C_2-C_6$-alkenylsulfonyl, and of which 2 alkyl groups can also be linked to form an optionally substituted di- to deca-methylene ring in which a C atom can be replaced by a heteroatom and which can additionally contain one or two double bonds, by cyano-$C_1-C_3$-alkyl, epoxy-$C_2-C_6$-alkyl, trifluoromethyl, hydroxyiminomethyl or $C_1-C_4$-alkoxyiminomethyl, pentafluoroethyl, by $C_2-C_6$-alkenyl which can be substituted by hydroxyl, by $C_2-C_6$-alkynyl, by $C_3-C_7$-cycloalkyl or $C_3-C_7$-cycloalkylmethyl, in which two substituents the ring can also be substituted by hydroxyl, halogen, carboxyl, $C_1-C_6$-alkyloxycarbonyl or cyano and in which a C atom can be replaced by an oxygen atom, by $C_4-C_7$-cycloalkenyl, by $C_1-C_6$-alkoxy, which can be substituted by hydroxyl, carboxyl or $C_1-C_6$-alkyloxycarbonyl, by epoxy-$C_2-C_6$-alkoxy, by $C_2-C_6$-alkenyloxy or $C_2-C_6$-alkynyloxy, by halogen, cyano, hydroxyl or mercapto, by $C_1-C_6$-alkylthio, $C_1-C_6$-alkylsulfinyl or $C_1-C_6$-alkylsulfonyl, all of which can be substituted by hydroxyl in the alkyl part, by methylthio, methylsulfinyl or methylsulfonyl, all of which are substituted in the methyl part by carboxyl or $C_1-C_6$-alkyloxycarbonyl, by $C_2-C_6$-alkenylthio, $C_2-C_6$-alkenylsulfinyl or $C_2-C_6$-alkenylsulfonyl, by phenyl, benzyl or heteroaryl, all of which can also be substituted by halogen, by formyl or ketalized formyl, by $C_1-C_6$-alkylcarbonyl which can also be substituted by hydroxyl and can also be present in ketalized form, by arylcarbonyl or $C_1-C_6$-alkylcarbonylamino, by carboxyl or $C_1-C_6$-alkoxycarbonyl, by carbamoyl which can be monosubstituted on the nitrogen by $C_1-C_6$-alkyl, hydroxy-$C_1-C_6$-alkyl, $C_1-C_6$-alkyloxycarbonyl, $C_1$–$C_6$-alkylcarbonyl, carboxymethyl, $C_1$–$C_6$-alkyloxycarbonylmethyl, aminocarbonylmethyl, $C_1$–$C_6$-alkylaminocarbonyl, carbamoyl, hydroxyl or pyridyl, or which can be disubstituted on the nitrogen by $C_1$–$C_6$-alkyl, by carbazoyl which can be substituted by $C_1$–$C_4$-alkyl, or N-carbamoylcarbazoyl, by sulfamoyl which can be monosubstituted on the nitrogen by $C_1$–$C_6$-alkylaminocarbonyl, or by pyridyl or 4-pyridon-1-yl, and in which preferred compounds of the general formula I the $R^2(A)_m(CH_2)_nO$— group is also in the syn position.

Optionally possible substituents for the di- to decamethylene ring mentioned under B, in which a C atom can be replaced by a heteroatom and one or two double bonds can additionally be contained, are in particular the following substituents, which can occur once or several times but preferably occur once: $C_1$–$C_6$-alkyl, $C_1$–$C_4$-alkoxy, hydroxymethyl, halogen, hydroxyl, oxo, hydroxyimino, exomethylene, carboxyl, $C_1$–$C_6$-alkyloxycarbonyl, cyano or carbamoyl.

These substituents can occur in the rings which have been mentioned and are fused onto the pyridinium radical, regardless of whether the particular ring is saturated, unsaturated, or additionally, interrupted by a heteroatom. However, according to the invention the substituents preferably occur on fused-on saturated rings which do not contain any heteroatoms.

The ring fused on the pyridinium radical can contain 2 to 10 ring members (di- to deca-methylene), but it preferably contains 3 to 5 ring members and it can thus be, for example, a cyclopenteno, cyclohexeno or cyclohepteno ring. If such a fused-on ring contains a double bond, then examples which may be mentioned are a cyclopentadieno, cyclohexadieno or cycloheptadieno ring. If in such rings a C atom is replaced by a heteroatom, the latter can be in particular oxygen or sulfur. Examples which may be mentioned of fused-on rings which contain an oxygen atom and two or one double bonds are furo, pyrano, dihydrofuro and dihydropyrano, and examples of fused-on rings which have a sulfur atom and contain two or one double bonds are thieno, thiopyrano, dihydrothieno and dihydrothiopyrano. Among the fused-on rings which contain a heteroatom, candidates of a substitution, in particular by the abovementioned substituents, are in particular those rings which contain only one double bond.

Examples of particularly preferable substituents are: $R_1$: hydrogen, bromine, chlorine and fluorine, in particular chlorine and bromine, $R_2$: the group —$CO_2R^3$ in which $R^3$ denotes hydrogen, $C_1$–$C_4$-alkyl, such as, for example, methyl, ethyl, propyl, isopropyl, butyl, sec.-butyl, tert.-butyl, preferably methyl, ethyl, in particular methyl, or one equivalent of an alkali metal, such as, for example, sodium, potassium, lithium, preferably sodium and potassium, one equivalent of an alkaline earth metal, preferably calcium or magnesium, of ammonium, and one equivalent of an organic amine base, such as, for example, trimethylamine, diethylamine, triethylamine, methylamine, propylamine, N,N-dimethylethanolamine, tris(hydroxymethyl)-aminomethane, arginine or lysine, a nitrile group, a carbamoyl group which can be monosubstituted at the nitrogen by $C_1$–$C_6$-alkyl, hydroxy-$C_1$–$C_6$-alkyl, $C_1$–$C_6$-alkyloxycarbonyl, $C_1$–$C_6$-alkylcarbonyl, carboxymethyl, $C_1$–$C_6$-alkyloxycarbonylmethyl, aminocarbonylmethyl, $C_1$–$C_6$-alkylaminocarbonyl, carbamoyl, hydroxyl, $C_1$–$C_6$-alkyloxy or which can be disubstituted at the nitrogen by $C_1$–$C_6$-alkyl, A: an aryl radical, preferably a phenyl radical, the group

in which $R^4$ and $R^5$ can be identical or different and can denote hydrogen, aryl, preferably phenyl, $C_1$–$C_4$-alkyl, such as, for example, methyl, ethyl, propyl, isopropyl, butyl, sec.-butyl, preferably methyl, ethyl, in particular methyl, or in which $R^4$ and $R^5$, together with the carbon atom to which they are bonded, can form a methylene group or a $C_3$–$C_7$-cycloalkylidene group, such as, for example, cyclopropyl, cyclobutyl, cyclopentyl, cyclohexyl, cycloheptyl, preferably cyclopropyl, cyclobutyl, cyclopentyl or cyclohexyl, and in which the cycloalkylidene group can be substituted, for example by $C_1$–$C_4$-alkyl, preferably methyl, by halogen, preferably fluorine and chlorine, or can also be substituted by alkylene having 3–6C atoms, l=0 or 1, preferably 0, m=0 or 1, n=0 or 1, with the sum of m and n being 1 or 2.

Preferable examples of the group —$(CH_2)_n(A)_m$— are the following:

In the event that n=0 and m=1:

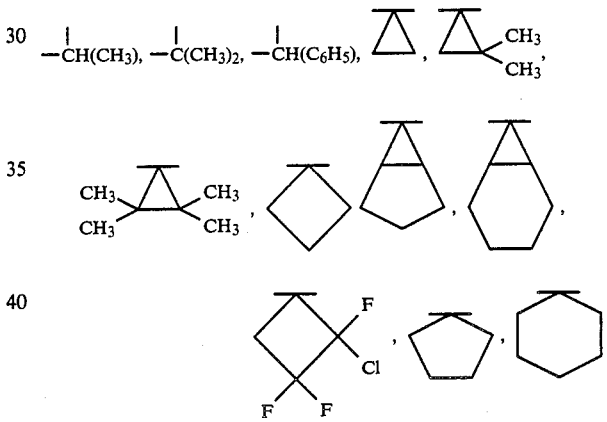

in the event that m=0 and n=1: —$CH_2$—, and if n and m=1:

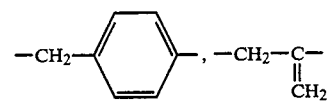

B: a pyridinium radical which can be monosubstituted or polysubstituted, preferably 1- to 3-fold, in particular 1- to 2-fold, for example by $C_1$–$C_4$-alkyl, such as, in particular, methyl, ethyl, propyl, isopropyl, n-butyl, sec.-butyl, tert.-butyl, dimethyl, trimethyl, methyl and ethyl, methyl and propyl, methyl and isopropyl, ethyl and ethyl, hydroxy-$C_1$–$C_4$-alkyl, such as in particular, hydroxymethyl, hydroxyethyl, hydroxypropyl, hydroxyisopropyl, hydroxybutyl, hydroxy-sec.-butyl or hydroxy-tert.-butyl, and in which it is also possible, for example, for two or three hydroxyl groups to be present on the alkyl radical, carboxy-$C_1$–$C_4$-alkyl, such as, in particular, carboxymethyl and carboxyethyl, $C_1$–$C_4$-alkyloxycarbonyl-$C_1$–$C_4$-alkyl, such as, in particular, methyloxycarbonylmethyl, ethyloxycarbonylmethyl, methyloxycarbonylethyl, formyl-$C_1$-$C_4$-alkyl, such as in particular, formylmethyl, $C_1$-$C_4$-alkylcarbonyl-$C_1$-$C_4$-alkyl, such as, in particular, methylcarbonylmethyl, ethylcarbonylmethyl, methylcarbonylethyl and ethylcarbonylethyl, the two alkyl groups of which can also be further substituted by hydroxyl and the carbonyl group of which can also be present in the ketalized form, carbamoyl-$C_1$-$C_4$-alkyl, such as, in particular, carbamoylmethyl and carbamoylethyl, which can also be further substituted by hydroxyl on the nitrogen, such as, in particular, N-hydroxycarbamoylmethyl, sulfo-$C_1$-$C_4$-alkyl, such as, in particular, sulfoethyl or 1-hydroxy-1-sulfomethyl, $C_1$-$C_4$-alkyloxy-$C_1$-$C_4$-alkyl, such as, in particular, methoxymethyl, ethoxymethyl, propoxymethyl, isopropoxymethyl, methoxyethyl, ethoxyethyl, methoxypropyl and methoxyisopropyl, all of which can also be substituted by hydroxyl, such as, in particular, hydroxyethoxymethyl and hydroxyethoxyethyl, $C_1$-$C_4$-alkylthio-$C_1$-$C_4$-alkyl, such as, in particular, methylthiomethyl, ethylthiomethyl, methylthioethyl and ethylthioethyl, $C_1$-$C_4$-alkylsulfinyl-$C_1$4 $C_4$-alkyl, such as, in particular, methylsulfinylmethyl, ethylsulfinylmethyl, methylsulfinylethyl and ethylsulfinylethyl, $C_1$-$C_4$-alkylsulfonyl-$C_1$-$C_4$-alkyl, such as, in particular, methylsulfonylmethyl, ethylsulfonylmethyl, methylsulfonylethyl and ethylsulfonylethyl, $C_3$-alkenyloxy-$C_1$-$C_4$-alkyl, such as, in particular, allyloxymethyl and allyloxyethyl, $C_3$-alkenylthio-$C_1$-$C_4$-alkyl, such as, in particular, allylthiomethyl, $C_3$-alkenylsulfinyl-$C_1$-$C_4$-alkyl, such as, in particular, allylsulfinylmethyl, $C_3$-alkenylsulfonyl-$C_1$-$C_4$-alkyl, such as, in particular, allylsulfonylmethyl, cyano-$C_1$-$C_3$-alkyl, such as, in particular, cyanomethyl and cyanoethyl, epoxy-$C_2$-$C_3$-alkyl, such as, in particular, epoxyethyl and epoxypropyl, trifluoromethyl, hydroxyiminomethyl and $C_1$-$C_3$-alkoxyiminomethyl, such as, in particular, methoxyiminomethyl, $C_3$-$C_4$-alkenyl, such as, in particular, allyl, 2-methylallyl and buten-3-yl, all of which can also be further substituted by hydroxyl, such as, in particular, hydroxyallyl and hydroxybutenyl, $C_3$-alkynyl, such as, in particular, propargyl, $C_3$-$C_6$-cycloalkyl and $C_3$-$C_6$-cycloalkylmethyl, in which the number of carbons relates to the cycloalkyl part, such as, in particular, cyclopropyl, cyclobutyl, cyclopentyl, cyclohexyl and cyclopentylmethyl, in which the rings can also be substituted, for example, by hydroxyl, such as, in particular, 1-hydroxy-1-cyclopentyl and 1-hydroxy-1-cyclohexyl, or by halogen, preferably chlorine, by carboxyl, $C_1$-$C_4$-alkoxycarbonyl or cyano, $C_5$-$C_6$-cycloalkenyl, such as, in particular, cyclopenten-1-yl and cyclohexen-1-yl, $C_1$-$C_4$-alkoxy, such as, in particular, methoxy ethoxy, propoxy, isopropoxy, butoxy, isobutoxy and tert.-butoxy, preferably methoxy, all of which alkoxy groups can also be further substituted, for example, by hydroxyl, carboxyl or $C_1$-$C_4$-alkoxycarbonyl, in particular carboxymethoxy and methoxycarbonylmethoxy, epoxy-$C_2$-$C_3$-alkoxy, such as, in particular, epoxyethoxy or epoxypropoxy, $C_3$-alkenyloxy, such as, in particular, allyloxy, $C_3$-alkynyloxy, such as, in particular, propargyloxy, halogen, such as, in particular, fluorine, chlorine, bromine or iodine, cyano, hydroxyl, in particular 3-hydroxy, $C_1$-$C_4$-alkylthio, such as, in particular, methylthio, ethylthio, propylthio and isopropylthio, all of which can also be substituted by hydroxyl, in particular hydroxyethylthio, $C_1$-$C_4$-alkylsulfinyl, such as, in particular, methylsulfinyl, ethylsulfinyl, propylsulfinyl and isopropylsulfinyl, all of which can also be substituted by hydroxyl, in particular hydroxyethylsulfinyl, $C_1$-$C_4$-alkylsulfonyl, such as methylsulfonyl, ethylsulfonyl, propylsulfonyl or isopropylsulfonyl, all of which can also be substituted by hydroxyl, in particular hydroxyethylsulfonyl, carboxymethylthio and $C_1$-$C_4$-alkoxycarbonylmethylthio, in particular methoxycarbonylmethylthio, carboxymethylsulfinyl and carboxymethylsulfonyl, $C_1$-$C_4$-alkoxycarbonylmethylsulfinyl and -alkoxycarbonylmethylsulfonyl, in particular methoxycarbonylmethylsulfinyl and methoxycarbonylmethylsulfonyl, $C_3$-alkenylthio, such as allylthio and propen-1-ylthio, $C_3$-alkenylsulfinyl, such as allylsulfinyl and propen-1-ylsulfinyl, $C_3$-alkenylsulfonyl, such as allylsulfonyl and propen-1-ylsulfonyl, phenyl and benzyl, both of which can also be substituted, for example by halogen, in particular chlorine, such as, for example, 4-chlorobenzyl, 2'-thienyl and 3'-thienyl, formyl and ketalized formyl, such as, for example, 1,3-dioxolan-2-yl, $C_1$-$C_4$-alkylcarbonyl, in particular acetyl and propionyl, preferably acetyl, which can also be substituted by hydroxyl and be present in ketalized form, such as, for example, 2-methyl-1,3-dioxolan-2-yl, benzoyl, $C_1$-$C_4$-alkylcarbonylamino, in particular acetylamino and propionylamino, formylamino, carboxyl, for example also 2,3,4-carboxyl, $C_1$-$C_4$-alkoxycarbonyl, in particular methoxycarbonyl and ethoxycarbonyl, such as, for example, also 2,3,4-methoxycarbonyl or 2,3,4-ethoxycarbonyl, carbamoyl (for example also 2,3,4-carbamoyl) which can be monosubstituted on the nitrogen atom by $C_1$-$C_4$-alkyl, such as, in particular, N-methylcarbamoyl and N-ethylcarbamoyl, by hydroxy-$C_1$-$C_4$-alkyl, such as, in particular, N-hydroxymethylcarbamoyl and N-hydroxyethylcarbamoyl, by $C_1$-$C_4$-alkoxycarbonyl, such as, in particular, N-methoxycarbonylcarbamoyl and N-ethoxycarbonylcarbamoyl, by $C_1$-$C_4$-alkylcarbonyl, such as, in particular, N-acetylcarbamoyl, by carboxymethyl, by $C_1$-$C_4$-alkoxycarbonylmethyl, such as in particular, N-methoxycarbonylmethylcarbamoyl and N-ethoxycarbonylmethylcarbamoyl, by aminocarbonylmethyl, by N-$C_1$-$C_4$-alkylaminocarbonyl, such as, in particular, N-methylaminocarbonylcarbamoyl and N-ethylaminocarbonylcarbamoyl by carbamoyl (=ureidocarbonyl), by hydroxyl or pyridyl, such as, in particular, N-3'-pyridylcarbamoyl and N-4'-pyridylcarbamoyl, N-$C_1$-$C_4$-dialkylcarbamoyl, such as, in particular, N,N-dimethylcarbamoyl and N,N-diethylcarbamoyl, carbazoyl which can be substituted by $C_1$-$C_4$-alkyl, in particular methyl or ethyl, by carbamoyl, such as N-carbamoylcarbazoyl, sulfamoyl, which can be substituted on the nitrogen atom by $C_1$-$C_4$-alkylaminocarbonyl, such as, in particular, ethylaminocarbonylsulfamoyl, and pyridyl, such as, in particular, 2'-, 3'- and 4'-pyridyl and 4-pyridon-1-yl.

If B represents a pyridinium radical which is substituted by two alkyl groups which are linked to form a di- to deca-methylene ring which in turn can be monosubstituted or polysubstituted but preferably is monosubstituted and can contain one or two double bonds, examples of this are in particular the following fused-on ring systems: cyclopenteno, hydroxycyclopenteno, chlorocyclopenteno, bromocyclopenteno, oxocyclopenteno, hydroxymethylcyclopenteno, exomethylenecyclopenteno, carboxycyclopenteno, $C_1$-$C_4$-alkoxycarbonylcyclopenteno, in particular methoxycarbonylcyclopenteno and carbamoylcyclopenteno, cyclohexeno, hydroxycyclohexeno, chlorocyclohexeno, bromocyclohexeno, oxocyclohexeno, hydroxymethylcyclohexeno, exomethylenecyclohexeno, carboxycyclohexeno, $C_1-C_4$-alkoxycarbonylcyclohexeno, in particular methoxycarbonylcyclohexeno and carbamoylcyclohexeno, cyclohepteno, hydroxy-, chloro-, bromo-, oxo-, hydroxymethyl-, exomethylene- or carboxy-cyclohepteno, $C_1-C_4$-alkoxycarbonylcyclohepteno, in particular methoxycarbonylcyclohepteno and carbamoylcyclohepteno, cyclopentadieno, cyclohexadieno and cycloheptadieno.

If in the abovementioned fused-on ring systems a C atom is replaced by a heteroatom, in particular oxygen or sulfur, possible examples are in particular: 2,3- and 3,4-furo, 2,3- and 3,4-pyrano, 2,3- and 3,4-dihydrofuro, 2,3- and 3,4-dihydropyrano, methyldihydrofuro, methoxydihydropyrano and hydroxydihydropyrano.

The invention also relates to a process for preparing compounds of the formula I and their physiologically acceptable acid addition salts, which process comprises reacting (a) a compound of the general formula II

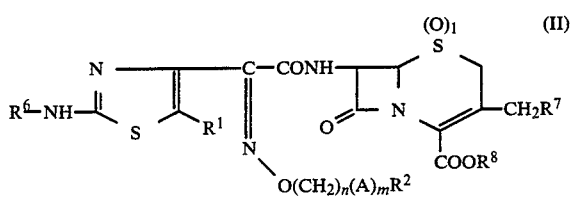

in which $R^1$, A, l, n and m have the abovementioned meanings and $R^2$ has the abovementioned meaning and in which, in the group $—CO_2R^3$, $R^3$ has the abovementioned meaning, or denotes an ester group readily detachable by acidic hydrolysis or hydrogenolysis, $R^6$ denotes hydrogen or an amino protective group, $R^7$ denotes a group which can be replaced by pyridine or substituted pyridines which correspond to the pyridinium radicals B of the formula I, and $R^8$ denotes a hydrogen atom or one equivalent of an alkali metal, alkaline earth metal, ammonium or of an organic amine base, with pyridine or a pyridine derivative which is such that it corresponds to one of the pyridinium radicals B mentioned in the formula I, whereupon, if the radicals $R^3$ and $R^6$ denote the abovementioned readily detachable groups, the latter are eliminated by treatment with an agent for acidic hydrolysis or hydrogenolysis or with thiourea and compounds of the formula I are thus obtained, or (b) reacting a 7-aminocephem compound of the general formula III

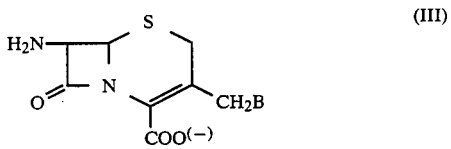

in which B has the meaning mentioned in the formula I, or its acid addition salts, in which the amino group can also be present in the form of a reactive derivative with a 2-(2-aminothiazol-4-yl)-2-syn-oximinoacetic acid of the general formula IV

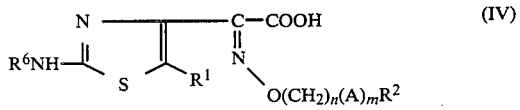

in which $R^1$, $R^2$, $R^6$, A, n and m have the abovementioned meaning and in which, if $R_2$ represents $COOR^3$, $R^3$ has the abovementioned meaning or denotes an ester group readily detachable by acidic hydrolysis or hydrogenolysis, with an activated derivative of this compound and ($\alpha$) eliminating a protective group, if present and ($\beta$) if necessary, converting the product obtained into a physiologically acceptable acid addition salt.

If the compounds of the general formula I are to be prepared by a nucleophilic replacement reaction of $R^7$ in the compounds of the general formula II by pyridine or one of the pyridine derivatives indicated, possible examples of radicals $R^7$ are in particular acyloxy radicals of lower aliphatic carboxylic acids, preferably having 1 to 4C atoms, such as, for example, acetoxy or propionyloxy, in particular acetoxy, which radicals may be substituted, such as, for example, chloroacetoxy or acetylacetoxy. Other groups are also possible for $R^7$ such as, for example, halogen, in particular chlorine or bromine, or carbamoyloxy.

Starting compounds of the general formula II in which $R^7$ represents acetoxy, or their salts, such as, for example, a sodium salt or potassium salt, are used, according to the invention, in the nucleophilic replacement reaction. The reaction is carried out in a solvent, preferably in water, or in a mixture of water and an organic solvent which is readily miscible with water, such as, for example, acetone, dioxane, acetonitrile, dimethylformamide, dimethylsulfoxide or ethanol. The reaction temperature is in general within the range from about 10° to about 100° C., preferably between 20° and 80° C. The pyridine component is added in amounts which are between approximately equimolar amounts and not more than an approximately 5-fold excess. The replacement of the radical $R^7$ is facilitated by the presence of neutral salt ions, preferably of iodide or thiocyanate ions, in the reaction medium. In particular, about 10 to about 30 equivalents of potassum iodide, sodium iodide, potassium thiocyanate or sodium thiocyanate are added. The reaction is advantageously carried out under approximately neutral conditions, preferably at a pH value within the range from about 5 to about 8.

If $R^7$ represents a carbamoyl group, the replacement reaction is carried out analogously. If $R^7$ represents halogen, in particular bromine, the replacement is effected in a manner described in the literature.

If the compounds of the formula II contain amino or acid protective groups in the radicals $R^3$ and $R^6$, the protective groups are eliminated after the nucleophilic replacement in a way which is in itself known by acidic hydrolysis, by hydrogenolysis or by means of thiourea.

Ester groups $R^3$ readily detachable by acidic hydrolysis or hydrogenolysis include, for example, tert.-butyl, tert.-amyl, benzyl, p-methoxybenzyl, p-nitrobenzyl and trichloroethyl. Examples of suitable amino protective groups $R^6$ are optionally substituted alkyl, such as, for example, tert.-butyl, tert.-amyl, benzyl, p-methoxybenzyl, trityl, benzhydryl, preferably trityl, trialkylsilyl, such as, for example, trimethylsilyl, optionally substituted aliphatic acyl, such as, for example, formyl, chloroacetyl, bromoacetyl, trichloroacetyl and trifluoroacetyl, preferably chloroacetyl, or optionally substituted alkoxycarbonyl, such as, for example, trichloroethoxycarbonyl, benzyloxycarbonyl, or tert.-butoxycarbonyl, preferably tert.-butoxycarbonyl and benzyloxycarbonyl, as well as 2-tetrahydropyranyl.

The acylation of the compounds of the general formula III or of their addition salts, for example with hydrochloric acid, hydrobromic acid, nitric acid, phosphoric acid or an organic acid, such as, for example, methanesulfonic acid or p-toluenesulfonic acid, can be carried out by means of carboxylic acids of the general formula IV or by means of a reactive derivative of such an acid. In this step, it is in some cases advantageous to protect the 2-amino group in the compounds of the general formula IV from the reaction by means of the abovementioned amino protective groups $R_6$.

After the acylation, the protective group can be split off in a manner which is in itself known, for example the trityl group by means of a carboxylic acid, such as, for example acetic acid, trifluoroacetic acid or formic acid, or the chloroacetyl group by means of thiourea.

If the carboxylic acids of the general formula IV and their derivatives protected at the amino group are themselves used as acylating agents, the reaction is advantageously carried out in the presence of a condensing agent, for example of a carbodiimide, such as, for example, N,N'-dicyclohexylcarbodiimide.

The activation of the carboxylic acid of the general formula IV can be particularly advantageously effected by treatment with certain carboxamides and, for example, phosgene, phosphorus pentachloride, tosyl chloride, thionyl chloride or oxalyl chloride, as described in German Patent No. 2,804,040.

Suitable activated derivatives of the carboxylic acids of the general formula IV are in particular also halides preferably chlorides, which can be obtained in a manner which is in itself known by treatment with halogenating agents, such as, for example, phosphorus pentachloride, phosgene or thionyl chloride, under mild reaction conditions described in cephalosporin chemistry literature.

Further suitable activated derivatives of the carboxylic acids of the general formula IV are the anhydrides and mixed anhydrides, azides and activated esters, preferably those formed with p-nitrophenol, 2,4-dinitrophenol, methylenecyanohydrin, N-hydroxysuccinimide and N-hydroxyphthalimide, in particular those formed with 1-hydroxybenzotriazole and 6-chloro-1-hydroxybenzotriazole. Particularly suitable mixed anhydrides are those formed with lower alkanoic acids, such as, for example, acetic acid, and particularly preferably those formed with substituted acetic acids, such as, for example, trichloroacetic acid, pivalic acid or cyanoacetic acid. However, those mixed anhydrides are also particularly suitable which are formed with carbonic acid half-esters, which are obtained, for example, by reacting the carboxylic acids of the formula IV, in which the amino group is protected, with benzyl chloroformate, p-nitrobenzyl chloroformate, isobutyl chloroformate, ethyl chloroformate or allyl chloroformate. The activated derivatives can be reacted as isolated substances or in situ.

Generally, the reaction of the cephem derivatives of the general formula III with a carboxylic acid of the general formula IV or with an activated derivative thereof is carried out in the presence of an inert solvent. Particularly suitable solvents are chlorinated hydrocarbons, such as preferably methylene chloride and chloroform, ethers, such as, for example, diethyl ether, preferably tetrahydrofuran and dioxane, ketones, such as preferably acetone and butanone, amides, such as preferably dimethylformamide and dimethylacetamide, or water. It can also be advantageous to use mixtures of the solvents mentioned. This can be advantageous in many cases where the cephem compound of the general formula III is reacted with an activated derivative of a carboxylic acid of the formula IV which derivative has been formed in situ.

The reaction of cephem compounds of the formula III with carboxylic acids of the formula IV or with activated derivatives thereof can be carried out within a temperature range of about 31 80° to about $+80°$ C., preferably between $-30°$ and $+50°$ C., but in particular between about $-20°$ C. and room temperature.

The reaction time depends on the reactants, the temperature and the mixture of solvents and normally is between about $\frac{1}{4}$ and about 72 hours.

The reaction with acid-halides may be carried out in the presence of an acid-binding agent to bind the hydrogen halide liberated. Suitable acid-binding agents are in particular tertiary amines, such as, for example, triethylamine or dimethylaniline, inorganic bases, such as, for example, potassium carbonate or sodium carbonate, or alkylene oxides, such as, for example, propylene oxide. The presence of a catalyst, such as, for example, of dimethylaminopyridine, may also be advantageous.

If in the compounds of the general formula III the amino group is present in the form of a reactive derivative, the latter can be of a type described in the literature for amidations. Possible examples are thus silyl derivatives which are formed when compounds of the general formula III are reacted with a silyl compound, such as, for example, trimethylchlorosilane or bis-(trimethylsilyl)-acetamide. If the reaction is carried out with one of these compounds which are activated at the amino group, it is advantageous to carry out the reaction in an inert solvent, such as, for example, methylene chloride, tetrahydrofuran or dimethylformamide.

Sulfoxides of the general formula I (l=1) are isolated in a manner which is in itself known by oxidation from cephalosporin derivatives of the general formula I in which l=0.

Suitable for the oxidation of the sulfur in the cephem ring are, for example, the methods described in the literature and which lead to the formation of SO and $SO_2$ bonds by oxidation of sulfides, as described, for example, in Methodicum Chimicum, volume 7 (1976), Hauptgruppenelemente und deren Verbindungen [Main group elements and their compounds], pages 693–698, by F. Korte, and the oxidizing agents mentioned in E. F. Flynn, Cephalosporins and Penicillins, Chemistry and Biology, Academic Press, New York and London, 1972, preferably the light-sensitized oxidation by means of oxygen, peroxides, hydroperoxides, peracids, singlet oxygen, hydrogen peroxide and mixtures thereof with inorganic or organic oxidation-resistant acids, such as, for example, phosphoric acid, formic acid, acetic acid or trifluoroacetic acid. The peracids can also be produced in situ by mixing of the acids with hydrogen peroxide. 3-Chloroperbenzoic acid is advantageously used directly.

Suitable solvents for the oxidation are all solvents stable under the reaction conditions, such as, for example, dioxane, tetrahydrofuran, chloroform, methylene chloride, acetic acid, formic acid, trifluoroacetic acid, glycol dimethyl ether, benzene, chlorobenzene, tetramethylurea, dimethylformamide and dimethylacetamide.

The reaction conditions and the amount of oxidizing agent depend on the final product desired and on the substituents present on the cephem skeleton. To prepare R- and S-sulfoxides, 2 oxidation equivalents (corresponding to one active oxygen atom) or a small excess are sufficient.

The reaction temperatures can be between about −20° and +80° C., but the oxidation is carried out at as low a temperature as possible, preferably −20° C. to +20° C.

In the oxidation of compounds of the formula I in which l represents 0 it is generally known that in the case of 7-acylaminocephem derivatives sulfoxides having S-configuration are predominantly formed.

R- and S-sulfoxides are separated and characterized owing to their differing solubility and their differing migration rate in chromatographic separations. A further distinction between R- and S-sulfoxides can be made with the aid of NMR spectroscopy (cf. the above-mentioned reference by E. H. Flynn).

Physiologically acceptable acid addition salts of compounds of the general formula I which may be mentioned by way of example are those salts formed with hydrochloric acid, hydrobromic acid, nitric acid, phosphoric acid or with organic acids, such as, for example, methanesulfonic acid or o-toluenesulfonic acid or maleic acid.

Compounds of the general formula III can be obtained in a manner which is in itself known, for example from 7-aminocephalosporanic acid protected at the amino group, in the way as described above for the nucleophilic replacement of $R^7$.

Compounds of the general formula IV and the pyridine derivatives which correspond to the pyridinium radicals B are known from the literature or can be prepared by methods described in the literature.

Compounds of the general formula I, obtained according to the invention, and their physiologically acceptable acid addition salts have remarkably high antibacterial actions, not only against Gram-positive but also again Gram-negative bacterial germs.

The compounds of the formula I are also unexpectedly highly active against penicillinase- and cephalosporinase-forming bacteria. Since these compounds additionally have favorable toxicological and pharmacological properties, they are valuable chemotherapeutic agents.

The invention thus also relates to medicaments for treating microbial infections and which contain one or more of the compounds according to the invention.

The products according to the invention can also be used in combination with other active compounds, for example of the series of the penicillins, cephalosporins or aminoglycosides.

The compound of the general formula I and their physiologically acceptable acid addition salts can be administered orally, intramuscularly or intravenously. Medicaments which contain one or more compounds of the general formula I as active compound can be prepared by mixing the compounds of the formula I with one or more pharmacologically acceptable excipients or diluents, such as, for example, fillers, emulsifiers, lubricants, taste corrigents, colorants or buffer substances and bringing the mixtures into a suitable galenic administration form, such as, for example, tablets, coated tablets, capsules or a solution or suspension suitable for parenteral administration.

Examples which may be mentioned of excipients or diluents are tragacanth, lactose, talc, agar-agar, polyglycols, ethanol and water. Preferaby suspensions or solutions in water are used for parenteral administration. It is also possible to administer the active compounds as such, without excipients or diluents, in a suitable form, for example in capsules.

Suitable doses of compounds of the general formula I or of their physiologically acceptable acid addition salts are from about 0.1 to 20 g per day, preferably 0.5 to 4 g per day, for an adult weighing about 60 kg.

Single, or in general, multiple doses can be administered, and the single dose can contain the active compound in an amount from about 50 to 1,000 mg, preferably from about 100 to 500 mg.

Cephem compounds of the formula I in which $R_1$ represents hydrogen, l represents 0, B represents pyridinium and $—(CH_2)_n(A)_mR^2$ represents $—CH_2COOR'$ ($R'=H$ or $C_{1-4}$alkyl) are known from German Offenlegungsschrift No. 3,037,101, while those with $R_1=H$, $l=0$, B=pyridinium or 3- or 4-carbamoylpyridinium and a radical

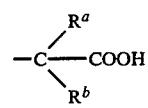

at the oximino group (with $R_{a,b}=C_{1-4}$-alkyl or $C_{3-7}$-cycloalkylidene) are known from German Offenlegungsschrift No. 2,921,316.

In addition to the products described in the illustrative examples, it is also possible to prepare, according to the invention, compounds which correspond to the general formula I′

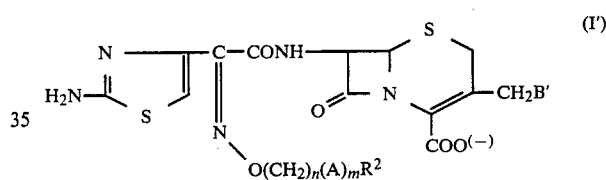

in which the radical $—(CH_2)_n(A)_mR^2$ has the above-mentioned meaning, preferably the following meanings —CH₂COOH     —CH₂—C COOH
—CH₂COOCH₃          ‖
—CH₂COOC₂H₅        CH₂
—CH₂CONH₂
—CH₂CN

—CH(CH₃)COOH
—C(CH₃)₂COOH

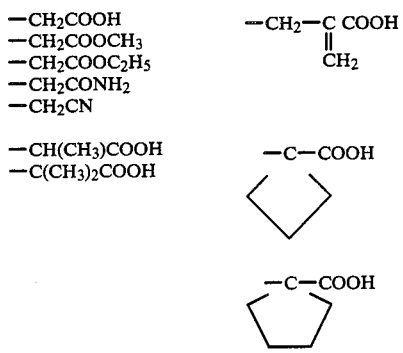

and is in the syn-position, and B′ (a) represents a pyridinium radical substituted by the radicals indicated in Table 1 or (b) denotes one of the radicals shown in Table 2.

In the formula I′, the meanings of B′ to be taken from Table 1 and 2 would thus have to be combined in each case in particular with the radicals mentioned above as preferable for $—(CH_2)_n(A)_mR^2$. Only for reasons of space has the replication of Tables 1 and 2, in itself necessary for each of these radicals of the oxime group, been omitted.

In Table 1, the numbers show the position of the substituent(s) on the pyridinium radical.

TABLE 1

| | | |
|---|---|---|
| 2,3-di-CH$_3$ | 3-Cyclobutyl | 2-(2-hydroxycyclohexyl) 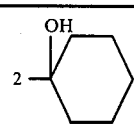 |
| 2,5-di-CH$_3$ | 4-Cyclobutyl | |
| 2-Propyl | 2-Cyclopentyl | |
| 3-Propyl | 3-Cyclopentyl | 3-(2-hydroxycyclohexyl) 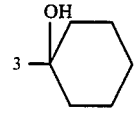 |
| 2-Isopropyl | 4-Cyclopentyl | |
| 2-n-Butyl | 2-Cyclopentylmethyl | |
| 3-n-Butyl | 3-Cyclopentylmethyl | 4-(2-hydroxycyclohexyl) 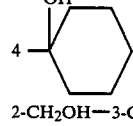 |
| 4-n-Butyl | 4-Cyclopentylmethyl | |
| 2-sec-Butyl | 2-Cyclohexyl | |
| 3-sec-Butyl | 3-Cyclohexyl | |
| 4-sec-Butyl | 4-Cyclohexyl | 2-CH$_2$OH—3-CH$_3$ |
| 2-tert-Butyl | 2-Cyclopentyl-3-CH$_3$ | 2-CH$_2$OH—4-CH$_3$ |
| 3-tert-Butyl | 2-Cyclopentyl-4-CH$_3$ | 2-CH$_2$OH—5-CH$_3$ |
| 2-C$_2$H$_5$—3-CH$_3$ | 2-Cyclopentyl-5-CH$_3$ | 3-CH$_2$OH—2-CH$_3$ |
| 2-C$_2$H$_5$—4-CH$_3$ | 3-Cyclopentyl-4-CH$_3$ | 3-CH$_2$OH—4-CH$_3$ |
| 2-C$_2$H$_5$—5-CH$_3$ | 3-Cyclopentyl-5-CH$_3$ | 3-CH$_2$OH—5-CH$_3$ |
| 3-C$_2$H$_5$—2-CH$_3$ | 4-Cyclopentyl-2-CH$_3$ | 3-CH$_2$OH—6-CH$_3$ |
| 3-C$_2$H$_5$—5-CH$_3$ | 4-Cyclopentyl-3-CH$_3$ | 4-CH$_2$OH—2-CH$_3$ |
| 4-C$_2$H$_5$—2-CH$_3$ | 2-(1-Cyclopenten-1-yl) | 4-CH$_2$OH—3-CH$_3$ |
| 4-C$_2$H$_5$—3-CH$_3$ | 3-(1-Cyclopenten-1-yl) | 2-CH$_2$OH—3-C$_2$H$_5$ |
| 2,3,4-triCH$_3$ | 4-(1-Cyclopenten-1-yl) | 2-CH$_2$OH—4-C$_2$H$_5$ |
| 2,3,5-triCH$_3$ | 2-(1-Cyclohexen-1-yl) | 2-CH$_2$OH—5-C$_2$H$_5$ |
| 2,4,5-triCH$_3$ | 3-(1-Cyclohexen-1-yl) | 3-CH$_2$OH—2-C$_2$H$_5$ |
| 3,4,5-triCH$_3$ | 4-(1-Cyclohexen-1-yl) | 3-CH$_2$OH—4-C$_2$H$_5$ |
| 2-CH$_2$CH=CH$_2$ | 2-CH$_2$C≡CH | 3-CH$_2$OH—5-C$_2$H$_5$ |
| 3-CH$_2$CH=CH$_2$ | 3-CH$_2$C≡CH | 3-CH$_2$OH—6-C$_2$H$_5$ |
| 4-CH$_2$CH=CH$_2$ | 4-CH$_2$C≡CH | 4-CB$_2$OH—2-C$_2$H$_5$ |
| 2-CH$_2$CH$_2$CH=CH$_2$ | 2-(2-hydroxycyclopentyl) 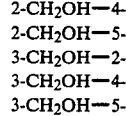 | 4-CH$_2$OH—3-C$_2$H$_5$ |
| 3-CH$_2$CH$_2$CH=CH$_2$ | | 2-CH$_2$OH—3,4-diCH$_3$ |
| 4-CH$_2$CH$_2$CH=CH$_2$ | | 2-CH$_2$OH—3,5-diCH$_3$ |
| 2-CH$_2$C(CH$_3$)=CH$_2$ | | 2-CH$_2$OH—4,5-diCH$_3$ |
| 3-CH$_2$C(CH$_3$)=CH$_2$ | 3-(2-hydroxycyclopentyl) 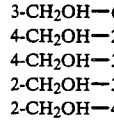 | 3-CH$_2$OH—2,4-diCH$_3$ |
| 4-CH$_2$C(CH$_3$)=CH$_2$ | | 3-CH$_2$OH—2,5-diCH$_3$ |
| 2-Cyclopropyl | | 3-CH$_2$OH—4,5-diCH$_3$ |
| 3-Cyclopropyl | 4-(2-hydroxycyclopentyl) 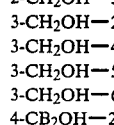 | 3-CH$_2$OH—4,6-diCH$_3$ |
| 4-Cyclopropyl | | 3-CH$_2$OH—5,6-diCH$_3$ |
| 2-Cyclobutyl | | 4-CH$_2$OH—2,3-diCH$_3$ |
| 4-CH$_2$OH—2,5-diCH$_3$ | 2-CH$_2$CH(OH)CH$_3$—4-CH$_3$ | |
| 4-CH$_2$OH—3,6-diCH$_3$ | 2-C(CH$_3$)$_2$OH—4-CH$_3$ | 3-CHCH$_2$CH=CH$_2$ 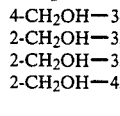 |
| 3-CH$_2$OH—4,5,6-triCH$_3$ | 3-C(CH$_3$)$_2$OH—6-CH$_3$ | |
| 2-CH$_2$CH$_2$OH | 4-C(CH$_3$)$_2$OH—3-CH$_3$ | 4-CHCH$_2$CH=CH$_2$ 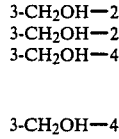 |
| 3-CH$_2$CH$_2$OH | 2-CH(CH$_3$)OH—4-C$_2$H$_5$ | |
| 4-CH$_2$CH$_2$OH | 2-CH$_2$CH$_2$OH—5-C$_2$H$_5$ | 2,3-di-CH$_2$OH |
| 2-CH$_2$CH$_2$OH—4-CH$_3$ | 3-CH(CH$_3$)OH—2,5-diCH$_3$ | 2,5-di-CH$_2$OH |
| 2-CH$_2$CH$_2$OH—3-CH$_3$ | 4-CH$_2$CH$_2$OH—3,5-diCH$_3$ | 2,4-di-CH$_2$OH |
| 2-CH$_2$CH$_2$OH—5-CH$_3$ | 2-CH(C$_3$H$_7$)OH | 3,4-di-CH$_2$OH |
| 3-CH$_2$CH$_2$OH—2-CH$_3$ | 3-CH(C$_3$H$_7$)OH | 3,5-di-CH$_2$OH |
| 3-CH$_2$CH$_2$OH—4-CH$_3$ | 4-CH(C$_3$H$_7$)OH | 2-CH$_2$OH—3-OH |
| 3-CH$_2$CH$_2$OH—5-CH$_3$ | 2-CH(C$_2$H$_5$)CH$_2$OH | 2-CH$_2$OH—3-OH—6-CH$_3$ |
| 3-CH$_2$CH$_2$OH—6-CH$_3$ | 3-CH(C$_2$H$_5$)CH$_2$OH | 2-CH—(CH$_2$OH)$_2$ |
| 4-CH$_2$CH$_2$OH—3-CH$_3$ | 4-CH(C$_2$H$_5$)CH$_2$OH | 3-CH(CH$_2$OH)$_2$ |
| 4-CH$_2$CH$_2$OH—2-CH$_3$ | 2-CH$_2$(CH$_2$)$_3$OH | 4-CH(CH$_2$OH)$_2$ |
| 2-CH(CH$_3$)OH—3-CH$_3$ | 3-CH$_2$(CH$_2$)$_3$OH | 3-C(CH$_2$OH)$_2$ |
| 2-CH(CH$_3$)OH—4-CH$_3$ | 4-CH$_2$(CH$_2$)$_3$OH | 4-C(CH$_2$OH)$_2$ |
| 2-CH(CH$_3$)OH—5-CH$_3$ | 2-CH(CH$_3$)CH$_2$CH$_2$OH | 2-CHOHCH$_2$OH |
| 3-CH(CH$_3$)OH—2-CH$_3$ | 3-CH(CH$_3$)CH$_2$CH$_2$OH | 3-CHOHCH$_2$OH |
| 3-CH(CH$_3$)OH—4-CH$_3$ | 4-CH(CH$_3$)CH$_2$CH$_2$OH | 4-CHOHCH$_2$OH |
| 3-CH(CH$_3$)OH—5-CH$_3$ | 2-C(C$_2$H$_5$)OH with CH$_3$ 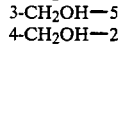 | 2-COCH$_2$OH |
| 3-CH(CH$_3$)OH—6-CH$_3$ | | 3-COCH$_2$OH |

TABLE 1-continued

| | | |
|---|---|---|
| 4-CH(CH₃)OH—2-CH₃ | CH₃ \| 3-C(C₂H₅)OH | 4-COCH₂OH |
| 4-CH(CH₃)OH—3-CH₃ | | CH₂OH \| 4-C(O—O) (cyclic) |
| 2-CH(C₂H₅)OH | | |
| 3-CH(C₂H₅)OH | CH₃ \| 4-C(C₂H₅)OH | 3-CH₂COCH₃ |
| 4-CH(C₂H₅)OH | | 2-CH₂COCH₃ |
| 2-CH(CH₃)CH₂OH | 2-CH₂C(CH₃)₂OH | 4-CH₂COCH₃ |
| 3-CH(CH₃)CH₂OH | 3-CH₂C(CH₃)₂OH | CH₃ \| 4-CH₂C(O—O) (cyclic) |
| 4-CH(CH₃)CH₂OH | 4-CH₂C(CH₃)₂OH | |
| 4-CH(CH₃)CH₂OH—5-CH₃ | 4-C(=CH₂)CH₂OH | |
| 2-(CH₂)₃OH | 3-C(=CH₂)CH₂OH | 3-CHCH₂COCH₃ \| OH |
| 3-(CH₂)₃OH | 2-C(=CH₂)CH₂OH | |
| 4-(CH₂)₃OH | 4-CH(OH)CH=CH₂ | 4-CHCH₂COCH₃ \| OH |
| 2-CH₂CH(OH)CH₃ | 2-CH(OH)CH=CH₂ | |
| 3-CH₂CH(OH)CH₃ | 3-CH(OH)CH=CH₂ | 4-CH—COCH₃ \| OH |
| 4-CH₂CH(OH)CH₃ | 2-CH(OH)CH₂CH=CH₂ | |
| 2-CH(O—O) (cyclic, dioxolane) | 2-OCH₃ | 2-butoxy |
| | 3-OCH₃ | 3-butoxy |
| 3-CH(O—O) | 2-OCH₃—3-CH₃ | 4-butoxy |
| | 2-OCH₃—4-CH₃ | 4-butoxy-2-CH₃ |
| | 2-OCH₃—5-CH₃ | 2-Isobutoxy |
| 4-CH(O—O) | 3-OCH₃—2-CH₃ | 3-Isobutoxy |
| | 3-OCH₃—4-CH₃ | 4-Isobutoxy |
| | 3-OCH₃—5-CH₃ | 2-tert butoxy |
| 2-C(O—O)CH₃ | 3-OCH₃—6-CH₃ | 3-tert butoxy |
| | 4-OCH₃—2-CH₃ | 4-tert butoxy |
| 3-C(O—O)CH₃ | 4-OCH₃—3-CH₃ | 2-OCH₂—CH=CH₂ |
| | 2-OC₂H₅ | 3-OCH₂—CH=CH₂ |
| | 3-OC₂H₅ | 4-O—CH₂—CH=CH₂ |
| 4-C(O—O)CH₃ | 4-OC₂H₅ | 2-OCH₂CH₂OH |
| | 2-OC₂H₅—3-CH₃ | 3-OCH₂CH₂OH |
| | 2-OC₂H₅—4-CH₃ | 4-OCH₂CH₂OH |
| | 2-OC₂H₅—5-CH₃ | 2-CH₂—OCH₃ |
| 4-CH—CH₂ (epoxide) | 3-OC₂H₅—2-CH₃ | 3-CH₂—OCH₃ |
| | 3-OC₂H₅—4-CH₃ | 3-CH₂OCH₃—2CH₃ |
| 3-CH—CH₂ (epoxide) | 3-OC₂H₅—5-CH₃ | 2-CH₂OC₂H₅ |
| | 3-OC₂H₅—6-CH₃ | 3-CH₂OC₂H₅ |
| 3-OCH₂—C—CH₂ (epoxide) | 4-OC₂H₅—2-CH₃ | 4-CH₂OC₂H₅ |
| | 4-OC₂H₅—3-CH₃ | 2-CH₂OC₃H₇ |
| 4-OCH₂—C—CH₂ (epoxide) | 2-OCH₃—4-C₂H₅ | 3-CH₂OC₃H₇ |
| | 4-OCH₃—2,5-diCH₃ | 4-CH₂OC₃H₇ |
| | 2-OCH(CH₃)₂ | 2-CH₂OCH(CH₃)₂ |
| | 3-OCH(CH₃)₂ | |
| 4-CH₂CHO | 4-OCH(CH₃)₂ | |
| 3-CH₂CHO | 4-OCH(CH₃)₂—2-CH₃ | |
| 2-CH₂CHO | | |

TABLE 1-continued

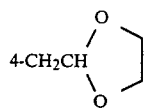

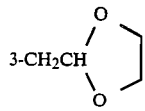

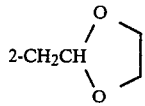

| | | |
|---|---|---|
| 3-CH₂OCH(CH₃)₂ | 3-OH—2-CH₃ | 3-SOCH₃ |
| 4-CH₂OCH(CH₃)₂ | 3-OH—4-CH₃ | 4-SOCH₃ |
| 2-CH₂OCH₂CH=CH₂ | 3-OH—5-CH₃ | 2-SO₂CH₃ |
| 3-CH₂OCH₂CH=CH₂ | 3-OH—6-CH₃ | 3-SO₂CH₃ |
| 4-CH₂OCH₂CH=CH₂ | 3-OH—2-C₂H₅—5-CH₃ | 4-SO₂CH₃ |
| 2-CH₂CH₂OCH=CH₂ | 3-OH—5-C₂H₅—2-CH₃ | 2-SC₂H₅ |
| 3-CH₂CH₂OCH=CH₂ | 3-OH—2-HC(CH₃)₂ | 3-SC₂H₅ |
| 4-CH₂CH₂OCH=CH₂ | 3-OH—2-CH₂CH₂CH₃ | 4-SC₂H₅ |
| 2-CH₂CH₂OCH₃ | 3-OH—2-butyl | 2-SOC₂H₅ |
| 3-CH₂CH₂OCH₃ | 3-OH—2-sec.butyl | 3-SOC₂H₅ |
| 4-CH₂CH₂OCH₃ | 3-OH—2-tert.butyl | 4-SOC₂H₅ |
| 3-CH₂CH₂OCH₃—4-CH₃ | 3-OH—4-butyl | 2-SO₂C₂H₅ |
| 2-CH₂CH₂OC₂H₅ | 3-OH—5-sec.butyl | 3-SO₂C₂H₅ |
| 3-CH₂CH₂OC₂H₅ | 3-OH—2,4,5-tri-CH₃ | 4-SO₂C₂H₅ |
| 4-CH₂CH₂OC₂H₅ | 3-OH—4,5,6-tri-CH₃ | 2-CH₂SCH₃ |
| 2-CH(OCH₃)CH₃ | 3-OH—6-CH=CH(CH₃) | 3-CH₂SCH₃ |
| 3-CH(OCH₃)CH₃ | 3-OH—2-CH=CH(CH₃) | 2-CH₂SOCH₃ |
| 4-CH(OCH₃)CH₃ | 3-OH—4-CH₂CH=CH₂ | 4-CH₂SOCH₃ |
| 2-CH(OC₂H₅)CH₃ | 3-OH—2-Cl | 2-CH₂SO₂CH₃ |
| 3-CH(OC₂H₅)CH₃ | 3-OH—5-Cl | 4-CH₂SO₂CH₃ |
| 4-CH(OC₂H₅)CH₃ | 3-OH—6-Cl | 2-CH₂SC₂H₅ |
| 2-(CH₂)₃OCH₃ | 3-OH—2-Br | 3-CH₂SC₂H₅ |
| 3-(CH₂)₃OCH₃ | 2-CH₂OCH₂CH₂OH | 4-CH₂SC₂H₅ |
| 4-(CH₂)₃OCH₃ | 3-CH₂O—CH₂CH₂OH | 2-CH₂SOC₂H₅ |
| 2-C(OCH₃)CH₃<br>  \|<br>  CH₃ | 4-CH₂OCH₂CH₂OH<br>2-(CH₂)₂OCH₂CH₂OH | 3-CH₂SOC₂H₅<br>4-CH₂SOC₂H₅ |
| 3-C(OCH₃)CH₃<br>  \|<br>  CH₃ | 3-(CH₂)₂OCH₂CH₂OH<br>4-(CH₂)₂OCH₂CH₂OH | 2-CH₂SO₂C₂H₅<br>3-CH₂SO₂C₂H₅ |
| 4-C(OCH₃)CH₃<br>  \|<br>  CH₃ | 2-OH<br>2-OH—3-CH₃ | 4-CH₂SO₂C₂H₅<br>4-SCH₂CH₂CH₃ |
| 3-OH—2-C₂H₅ | 2-OH—4-CH₃ | 3-SOCH₂CH₂CH₃ |
| 3-OH—4-C₂H₅ | 2-OH—5-CH₃ | 2-SO₂CH₂CH₂CH₃ |
| 3-OH—5-C₂H₅ | 4-OH | 2-SCH(CH₃)₂ |
| 3-OH—6-C₂H₅ | 4-OH—2-CH₃ | 3-SOCH(CH₃)₂ |
| 3-OH—2,4-di-CH₃ | 4-OH—3-CH₃ | 4-SO₂CH(CH₃)₂ |
| 3-OH—2,5-diCH₃ | 3-SCH₃ | 2-CH₂CH₂SCH₃ |
| 3-OH—4,5-diCH₃ | 4-SCH₃ | 3-CH₂CH₂SOCH₃ |
| 3-OH—4,6-diCH₃ | 2-SOCH₃ | 4-CH₂CH₂SO₂CH₃ |
| 2-CH₂CH₂SOC₂H₅ | 2-CF₃ | 6-CH₂OCH₃—3-Br |
| 3-CH₂CH₂SO₂C₂H₅ | 3-CF₃ | 2-CH₂OCH₃—3-Cl |
| 4-CH₂CH₂SC₂H₅ | 4-CF₃ | 4-CH₂OCH₃—3-Cl |
| 2-SCH₂CH₂OH | 3-J | 5-CH₂OCH₃—3-Cl |
| 3-SCH₂CH₂OH | 2-OCH₃—3-Br | 6-CH₂OCH₃—3-Cl |
| 4-SCH₂CH₂OH | 4-OCH₃—3-Br | 2-CH₂OCH₃—3-F |
| 2-SOCH₂CH₂OH | 5-OCH₃—3-Br | 4-CH₂OCH₃—3-F |
| 3-SOCH₂CH₂OH | 6-OCH₃—3-Br | 5-CH₂OCH₃—3-F |
| 4-SOCH₂CH₂OH | 2-OCH₃—3-Cl | 6-CH₂OCH₃—3-F |
| 2-SO₂CH₂CH₂OH | 4-OCH₃—3-Cl | |
| 3-SO₂CH₂CH₂OH | 5-OCH₃—3-Cl | |
| 4-SO₂CH₂CH₂OH | 6-OCH₃—3-Cl | |
| 2-SCH₂—CH=CH₂ | 2-OCH₃—3-F | |
| 3-SOCH₂CH=CH₂ | 4-OCH₃—3-F | |
| 4-SO₂CH₂CH=CH₂ | 5-OCH₃—3-F | |
| 2-S—CH=CH—CH₃ | 6-OCH₃—3-F | |
| 3-S—CH=CH—CH₃ | 3-F—5-OH | |
| 4-S—CH=CH—CH₃ | 3-Cl—5-OH | |
| 4-CH₂S—CH₂CH=CH₂ | 3-Br—5-OH | |
| | 3-J—5-OH | |
| | 2-CH₂OH—3-Br | |
| | 4-CH₂OH—3-Br | |
| | 5-CH₂OH—3-Br | |

TABLE 1-continued

6-CH$_2$OH—3-Br
2-CH$_2$OH—3-Cl
4-CH$_2$OH—3-Cl
5-CH$_2$OH—3-Cl
6-CH$_2$OH—3-Cl
2-CH$_2$OH—3-F
4-CH$_2$OH—3-F
5-CH$_2$OH—3-F
6-CH$_2$OH—3-F
5-OC$_2$H$_5$—3-Br
5-OC$_2$H$_5$—3-Cl
5-OC$_2$H$_5$—3-F
2-CH$_2$OCH$_3$—3-Br
4-CH$_2$OCH$_3$—3-Br
5-CH$_2$OCH$_3$—3-Br

TABLE 2

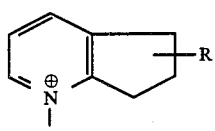 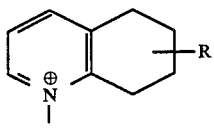 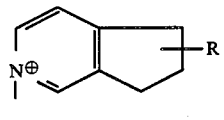

R = H
 = 7-OH
 = 7-OCH$_3$
 = 7-CH$_2$OH
 = 7,7-diCH$_2$OH
 = 7-Cl
 = 7-exo-methylene
 = 7-CONH$_2$
 = 3-OH = 3-CH$_2$OH
 = 4-CH$_3$
 = 3-CH$_3$
 = 4-CH$_2$OH
 = 5-OH, 7-CH$_3$
 = 6-OH, 7-CH$_3$
 = 5-CH$_3$
 = 6-CH$_3$
 = 7-CH$_3$ R = H
 = 8-CH$_3$
 = 8-OH
 = 8-OH, 3-CH$_3$
 = 8-CH$_2$OH
 = 8-CH$_2$OH, 3-CH$_3$
 = 8-OCH$_3$
 = 8,8-di-CH$_2$OH
 = 8-Cl = 8-Br
 = 8-exo-methylene = 8-CONH$_2$
 = 8-Oxo
 = 6-Cl
 = 5-OH
 = 5-oxo
 = 5-Cl
 = 3-CH$_2$OH

= 3-OH
 = 4-OCH$_3$
 = 2-CH$_3$

= 3-CH$_3$
 = 4-CH$_3$

R = H
 4-OH
 4-OCH$_3$
 1-Cl
 5-Cl

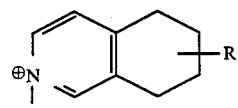

R = H
 = 4-OH

= 4-OCH$_3$
 = 2-Cl
 = 5-Cl

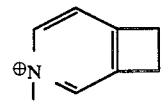

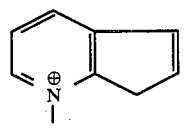

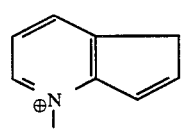

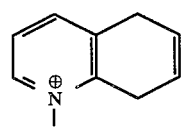

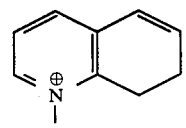

TABLE 2-continued
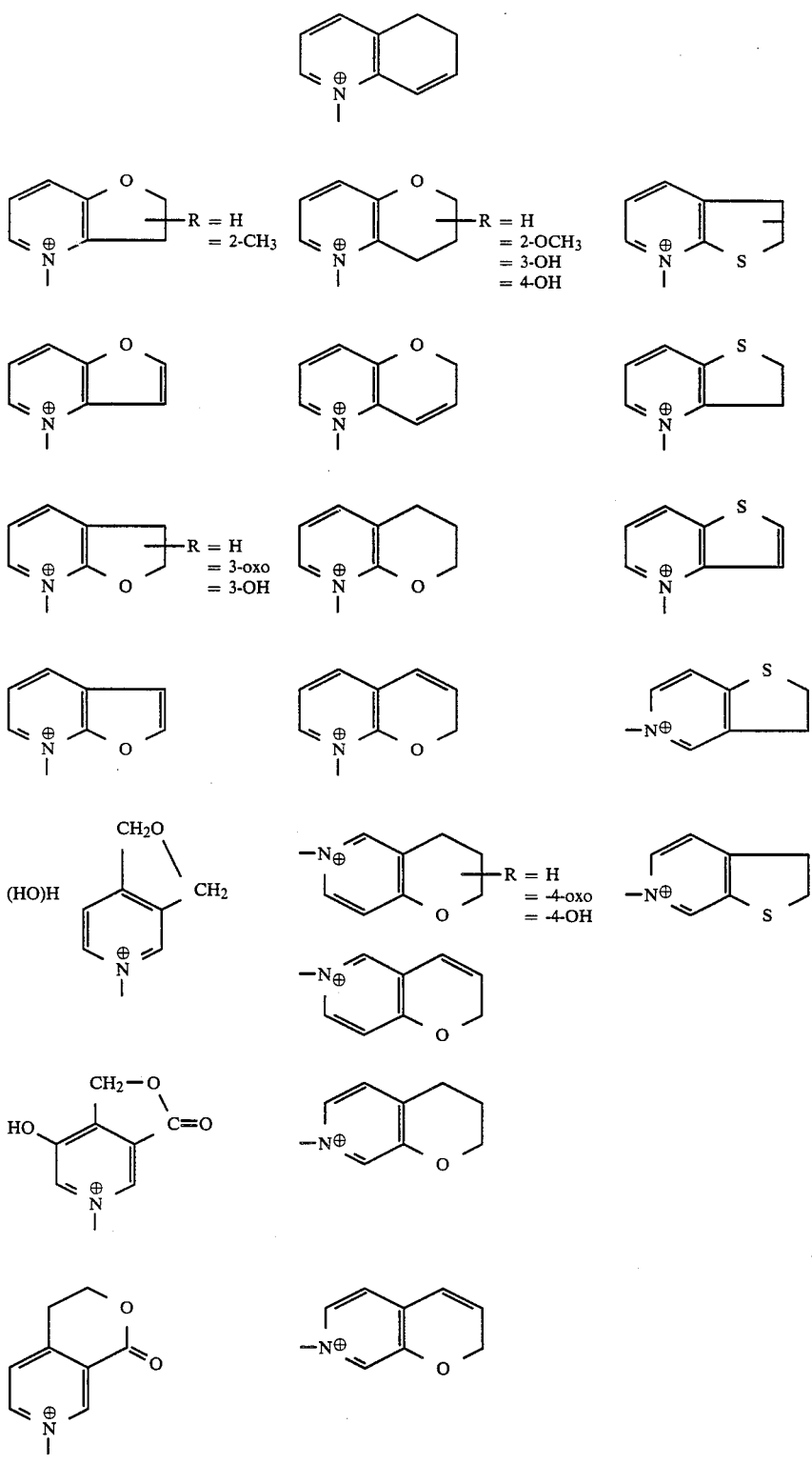
The illustrative examples below of syn compounds which can be prepared according to the invention serve to illustrate the invention in more detail but do not restrict it to these.

(a) Trifluoroacetate of (6R,7R)-3-acetoxymethyl-7-[(Z)-2-(2-aminothiazol-4-yl)-2-carboxymethyloxyimino-acetamido]-ceph-3-em-4-carboxylic acid A solution of 1.7 g (2 mmoles) of tert.-butyl(6R,7R)-3-acetoxymethyl-7-[(Z)-2-tert.-butoxycarbonylmethyloxyimino-2-(2-tritylaminothiazol-4-yl)acetamido]-ceph-3-em-4-carboxylate in 20 ml of trifluoroacetic acid was stirred for 30 minutes at room temperature. The solution was concentrated, and the residue was taken up in ether/n-pentane (2:1), filtered off with suction, washed with the same solvent mixture, and dried in air. The yield is quantitative. IR (KBr): 1800 cm$^{-1}$ (lactam-CO).

(b) Monopotassium salt of (6R,7R)-7-[(Z)-2-(2-aminothiazol-4-yl)-2-(carboxymethyloxyimino)-acetamido]-3-[(2,3-cyclopenteno-1-pyridinium)methyl]-ceph-3em-4-carboxylate

Process (a)

1.2 g (2 mmoles) of the product of stage (a) were suspended in 4 ml of water and dissolved by adding 0.6 g of potassium hydrogen carbonate. 3.9 g (40 mmoles) of potassium thiocyanate and 0.71 ml (6 mmoles) of 2,3-cyclopentenopyridine were then added, and the pH of the mixture was adjusted to 6.6 by means of 85% strength phosphoric acid. The mixture was heated for 3 hours at 65°–70° C. The mixture was diluted with 32 ml of acetone, a small amount of undissolved material was filtered off, and the filtrate was chromatographed over 200 g of silica gel (Merck 0.063–0.2 mm). The neutral salts were eluted with acetone/water (8:1), and the product was eluted with acetone/water (2:1). The freeze-dried crude product was re-chromatographed over silica gel (Merck, Lobar B column, Article No. 10,401, about 1 bar, acetone/water 2:1). Freeze-drying of the product fractions (fractions 7-10, 60 ml) produced 0.25 g (21% of theory) of the title compound in the form of a colorless solid.

IR (KBr): 1770 cm$^{-1}$ (lactam-CO).

$^1$H-NMR (CF$_3$CO$_2$D): δ = 2.3–2.8 (m, 2H, cyclopentene-H); 3.1–4.0 (m, 6H, 4 cyclopentene-H and SCH$_2$); 5.09 (s, 2H, OCH$_2$); 5.1–6.25 (m, 4H, CH$_2$Py and 2 lactam-H); 7.43 (s, 1H, thiazole); 7.65–8.65 ppm (m, 3H, Py).

EXAMPLE 2

Monosodium salt of (6R,7R)-7-[(Z)-2-(2-aminothiazol-4-yl)-2-(carboxymethyloxyimino)-acetamido]-3-[(4-cyclopropyl-1-pyridinium)methyl]-ceph-3-em-4-carboxylate

Process (b)

0.45 g (2.2 mmoles) of dicyclohexylcarbodiimide was added to a solution of 1.1 g (2 mmoles) of (Z)-2-(2-tert.-butoxycarbonylmethyloxyimino)-2-(2-tritylaminothiazol-4-yl)-acetic acid and 0.31 g (2 mmoles) of 1-hydroxy-1H-benzotriazole hydrate in 15 ml of N,N-dimethylformamide. After stirring for 2 hours at room temperature, the mixture was cooled down to −20° C., and a solution of 0.8 g (2 mmoles) of 7-amino-3-[(4-cyclopropyl-1-pyridiniummethyl]-ceph-3-em-4-carboxylate dihydrochloride and 0.6 g (5 mmoles) of N,N-dimethylaniline in 5 ml of N,N-dimethylformamide was added. The mixture was stirred for 2 hours and left to stand overnight at room temperature. The precipitate (dicyclohexylurea) was filtered off, and the filtrate was added dropwise with stirring to 200 ml of diethyl ether. The solids were filtered off, washed with ether and dried. The solid material was dissolved in 10 ml of trifluoroacetic acid. The solution was concentrated after 30 minutes, and the residue was taken up in either/n-pentane (2:1). The solids was filtered off, and washed with ether and dried. The solid material was suspended in 4 ml of water and dissolved by adding sodium bicarbonate. The solution was chromatographed over silica gel (Merck, Lobar C column Article No. 10,402, about 1 bar, acetone/water 2:1). The product fractions (fractions 26-36, 180 ml) were concentrated and freeze-dried. Yield: 0.23 g (20% of theory) of a colorless solid.

IR (KBr) 1770 cm$^{-1}$ (lactam-CO).

$^1$H-NMR (CF$_3$CO$_2$D): δ = 1.05–2.6 (m, 5H, cyclopropyl); 3.40 and 3.82 (AB, J = 18 Hz, 2H, SCH$_2$); 5.06 (s, 2H, OCH$_2$); 5.1–6.25 (m, 4H, CH$_2$Py and 2 lactam-H); 7.42 (s, 1H, thiazole); 7.63 and 8.65 ppm (AA'BB', 4H, Py).

EXAMPLE 3

(a) (Z)-2-(2-tert.-butoxycarbonyl-2-propen-1-yloxyimino)-2-(2-tritylaminothiazol-4-yl)-acetic acid 1.5 ml of water were added to a mixture of 9.6 g (85.6 mmoles) of potassium tert.-butylate and 17.2 g (40 mmoles) of (Z)-2-hydroxyimino-2-(2-tritylaminothiazol-4-yl)-acetic acid in 500 ml of tetrahydrofuran. An almost clear blue-colored solution was obtained after 30 minutes' stirring. 10.2 g (46 mmoles) of tert.-butyl 2-(bromomethyl)-acrylate (R. Lattrell and G. Lohaus, Liebigs Annalen der Chemie, 1974, 870) were added, and the color of the solution changed from blue to red-brown within 10 minutes. The solution was concentrated at room temperature after stirring for 2 hours, and the residue was dissolved in 400 ml of ethyl acetate/water (1:1).

The aqueous phase was adjusted to pH 2 by means of 1N hydrochloric acid and extracted 3× with ethyl acetate. The combined organic phases were dried with sodium sulfate, and filtered, the filtrate was concentrated, and the residue was triturated with n-pentane. The undissolved red-brown product was filtered off with suction and dried in air. Yield: 17.2 g (76% of theory).

(b) Monosodium salt of (6R,7R)-7-[(Z)-2-(2-aminothiazol-4-yl)-(2-carboxy-2-propen-1-yloxyimino)-acetamido]-3-[(2,3-cyclopenteno-1-pyridinium)methyl]-ceph-3-em-4-carboxylate

Process (b)

A mixture of 4 ml of a 2 molar solution of phosgene in toluene (8 mmoles) and 2.0 ml of N,N-dimethylacetamide was added at −20° C. to a solution of 4 g (7 mmoles) of the product of stage (a) and 0.95 ml (7.1 mmoles) of triethylamine in 5 ml of N,N-dimethylacetamide. The mixture was stirred for 1 hour at −10° C., and this solution was then stirred into a cooled suspension at −60° C. of 3.3 g (8 mmoles) of 7-amino-3-[(2,3-cyclopenteno-1-pyridinium)methyl]-ceph-3-em-4-carboxylate dihydrochloride and 3 ml (22 mmoles) of triethylamine in 20 ml of methylene chloride. The mixture was stirred for 1 hour at −20° C. The phases were separated after 20 ml of water had been added, and the aqueous phase was extracted two more times with methylene chloride. The organic phase was dried with sodium sulfate and filtered, and the solvent was removed in vacuo. The residue was dissolved in 30 ml of trifluoroacetic acid, and the solution was stirred for 30 minutes at room temperature. It was concentrated, triturated with ether/n-pentane (2:1), filtered with suction, and the solids retained were dried. The crude product was dissolved in 5 ml of water with the addition of sodium bicarbonate and and chromatographed over silica gel (Merck, Lobar C column, about 1 bar, acetone/water 2:1). The product fractions (fractions 45–60, 250 ml) were concentrated and freeze-dried. 450 mg (11% of theory) of the title compound are obtained in the form of a colorless solid.

IR (KBr): 1775 cm$^{-1}$ (lactam-CO).

$^1$H-NMR (CF$_3$CO$_2$D): δ=2.3–2.8 (m, 2H, cyclopentene-H); 3.13–4.0 (m, 6H, 4 cyclopentene-H and SCH$_2$); 5.1–6.4 (m, 6H, N—O—CH$_2$ to 5.20, CH$_2$Py and 2 lactam-H); 6.6–6.95 (m, 2H, C=CH$_2$); 7.42 (s, 1H, thiazole); 7.65–8.66 ppm (m, 3H, Py).

The compounds listed below, and which correspond to the general formula I with l=0 and R$^1$=hydrogen, were obtained analogously to Example 1, 2 and 3.

TABLE 3

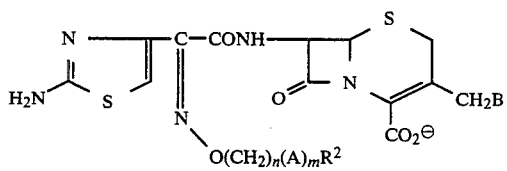

| Example | (CH$_2$)$_n$(A)$_m$R$^2$ | B | Process Yield as % of theory | $^1$H—NMR: δ (ppm) in CF$_3$CO$_2$D |
|---|---|---|---|---|
| 4 | —CH$_2$CO$_2$K | | a(18) | 2.1–2.8(m, cyclopentene-H); 3.0–4.0(m, 6H, 4 cyclopentene-H and SCH$_2$); 4.95–6.4(m, 6H, OCH$_2$ to 5.06, CH$_2$Py and 2 lactam-H); 7.42(s, 1H, thiazole); 7.77–8.9(m, 3H, Py) |
| 5 | —CH$_2$CO$_2$K | | a(21) | 1.83–2.42(m, 4 cyclohexene-H); 2.9–3.4(m, cyclohexene-H); 3.40 amd 3,73(AB, J=18Hz, 2H, SCH$_2$); 5.06(s, 2H, OCH$_2$); 5.2–6.2(m, 4H, CH$_2$Py and 2 lactam-H); 7.42(s, 1H, thiazole); 7.6–8.75(m, 3H, Py) |
| 6 | —CH$_2$CO$_2$K | | a(22) | 1.8–2.65(m, 4 cyclohenene-h); 2.8–3.35 (m, 4 cyclohexene-H); 3.40 and 3.82(AB, J= 18Hz, 2H, SCH$_2$); 5.05(s, 2H, OCH$_2$); 5.15–6.3(m, 4H, CH$_2$Py and 2 lactam-H); 7.43(s, 1H, thiazole); 7.6–8.7(m, 3H, Py) |
| 7 | —CH$_2$CO$_2$K | | a(24) | 1.9–2.5(m, 2 pyran-H); 2.8–3.5(m, 2 pyran-H); 3.41 and 3.81(AB, J=19Hz), 2H, SCH$_2$); 4.45–4.85(m, 2 pyran-H); 4.9–6.35(m, 6H, OCH$_2$ to 5.08, CH$_2$Py and 2 lactam-H); 7.15–7.5(m, 2H, thiazole-H to 7.42 and Py—H); 8.3–8.7(m, 2H, Py) |
| 8 | —CH$_2$CO$_2$K | | a(26) | 1.55–2.25(m, 6H, cycloheptene-H); 3.03–3.7 (m, 6H, SCH$_2$ and 4 cycloheptene-H); 5.08(s, 2H, OCH$_2$); 5.1–6.36(m, 4H, CH$_2$Py and 2 lactam-H); 7.43(s, 1H, thiazole); 7.55–8.75 (m, 2H, Py) |
| 9 | —CH$_2$CO$_2$K | | a(26) | 2.15–3.85(m, 6H, 4 cyclopentene-H, SCH$_2$) 4.95–6.35(m, 7H, OCH$_2$ to 5.05, 1 cyclopentene-H, CH$_2$Py and 2 lactam-H); 7.41(s, 1H, thiazole); 7.8–8.95(m, 3H, Py) |
| 10 | —C(CH$_3$)$_2$CO$_2$K | | a(24) | 1.79(s, 6H, 2 × CH$_3$); 2.3–2.85(m, 2 cyclopentene-H); 3.1–3.9(m, 6H, 4 cyclopentene-H and SCH$_2$); 5.25–6.25(m, 4H, CH$_2$Py and 2 lactam-H); 7.40(s, 1H, thiazole); 7.6–8.7(m, 3H, Py) |
| 11 | —C(CH$_3$)$_2$CO$_2$K | | a(26) | 1.80(s, 6H, 2 × CH$_3$); 2.25–2.7(m, 2 cyclopentene-H); 3.05–4.05(m, 6H, 4 cyclopentene-H and SCH$_2$); 5.15–6.35(m, 4H, CH$_2$Py and 2 lactam-H); 7.41(s, 1H, thiazole); 7.63–8.85(m, 3H, Py) |

TABLE 3-continued

Structure at top:
$H_2N$—(thiazole with S, N)—C(=NOR')—CONH—(β-lactam)—N—CH$_2$B, with CO$_2^\ominus$, and =N—O(CH$_2$)$_n$(A)$_m$R$^2$

| Example | (CH$_2$)$_n$(A)$_m$R$^2$ | B | Process Yield as % of theory | $^1$H—NMR: δ (ppm) in CF$_3$CO$_2$D |
|---|---|---|---|---|
| 12 | —C(CH$_3$)$_2$CO$_2$K | 5,6,7,8-tetrahydroquinolinium | a(19) | 1.65–2.4(m, 10H, 4 cyclohexene-H and 2 × CH$_3$ to 1.79); 2.95–4.05(m, 6H, 4 cyclohexene-H and SCH$_2$); 5.25–6.25(m, 4H, CH$_2$Py and 2 lactam-H); 7.40(s, 1H, thiazole); 7.6–8.65(m, 3H, Py) |
| 13 | —C(CH$_3$)$_2$CO$_2$K | 6,7-dihydro-5H-cyclopenta[b]pyridinium | a(21) | 1.65–2.35(m, 10H, 4 cyclohexene-H and 2 × CH$_3$ to 1.80); 2.8–3.4(m, 4 cyclohexene-H); 3.43 and 3.83(AB, J=18Hz, 2H, SCH$_2$); 5.15–6.36(m, 4H, CH$_2$Py and 2 lactam-H); 7.40(s, 1H, thiazole); 7.6–8.8(m, 3H, PY) |
| 14 | —C(CH$_3$)$_2$CO$_2$K | chromeno-pyridinium (with O) | a(18) | 1.80(s, 6H, 2 × CH$_3$); 1.9–2.5(m, 2 pyran-H); 2.83–3.16(m, 2 pyran-H); 3.42 and 3.79(AB, J=19Hz, 2H, SCH$_2$); 4.45–4.75(m, 2-pyran-H); 4.95–6.25(m, 4H, CH$_2$Py and 2 lactam-H); 7.15–7.45(m, 2H, thiazole-H to 7.40 and Py—H) 8.3–8.65(m, 2H, Py) |
| 15 | —C(CH$_3$)$_2$CO$_2$K | 3-methyl-5,6,7,8-tetrahydroquinolinium | a(21) | 1.65–2.35(m, 10H, 4 cyclohexene-H and s of (CH$_3$)$_2$ to 1.80); 2.54(s, 3H, CH$_3$); 2.8–3.75(m, 6H, 4 cyclohexene-H and SCH$_2$); 5.2–6.28(m, 4H, CH$_2$Py and 2 lactam-H); 7.41(s, 1H, thiazole); 8.11 and 8.41 (1H, bs, Py each) |
| 16 | —OCH(CH$_3$)—COOK | 6,7-dihydro-5H-cyclopenta[b]pyridinium | a(26) | 1.73(d, J=7Hz, 3H, CH$_3$); 2.2–2.9(m, 2 cyclopentene-H); 3.1–4.1(m, 6H, 4 cyclopentene-H and SCH$_2$); 4.95–6.4(m, 5H, C$\underline{H}$—CH$_3$, CH$_2$Py and 2 lactam-H); 7.42(s, 1H, thiazole); 7.63–8.72(m, 3H, Py) |
| 17 | —CH$_2$CO$_2$CH$_3$ | 6,7-dihydro-5H-cyclopenta[b]pyridinium | a(16) | 2.35–2.9(m, 2 cyclopentene-H); 3.1–3.85 (m, 6H, 4 cyclopentene-H and SCH$_2$); 3.96 (s, 3H, CH$_3$); 5.02(s, 2H, OCH$_2$); 5.16–6.4(m, 4H, CH$_2$Py and 2 lactam-H); 7.41 (s, 1H, thiazole); 7.6–8.7(m, 3H, Py) |
| 18 | —CH$_2$CO$_2$C$_2$H$_5$ | 6,7-dihydro-5H-cyclopenta[b]pyridinium | a(22) | 1.41(t, J=7Hz, 3H, CH$_2$C$\underline{H_3}$); 2.15–2.85(m, 2H, cyclopentene-H); 2.95–3.75(m, 6H, 4 cyclopentene-H and SCH$_2$); 4.42(q, J=7Hz, 2H, C$\underline{H_2}$CH$_3$); 4.9–6.2(m, 6H, OCH$_2$ to 5.02, CH$_2$Py and 2 lactam-H); 7.42(s, 1H, thiazole); 7.65–8.72(m, 3H, Py) |
| 19 | —CH$_2$CN | 6,7-dihydro-5H-cyclopenta[b]pyridinium | a(24) | 2.17–2.83(m, 2H, cyclopentene-H); 2.95–3.85 (m, 6H, 4-cyclopentene-H and SCH$_2$); 5.02–6.21 (m, 6H, OCH$_2$—s to 5.13, CH$_2$Py and 2 lactam-H) 7.45(s, 1H, thiazole); 7.65–8.72(m, 3H, Py) |
| 20 | —CH$_2$CONH$_2$ | 6,7-dihydro-5H-cyclopenta[b]pyridinium | a(31) | 2.18–2.81(m, 2H, cyclopentene-H); 3.05–3.95 (m, 6H, 4 cyclopentene-H and SCH$_2$); 4.92–6.25(m, 6H, OCH$_2$, CH$_2$Py and 2 lactam-H); 7.46(s, 1H, thiazole); 7.66–8.75(m, 3H, Py) |

TABLE 3-continued

[Structure: thiazole-aminothiazole with oxime O(CH₂)ₙ(A)ₘR², amide linked to β-lactam with CH₂B group and CO₂⁻]

| Example | (CH₂)ₙ(A)ₘR² | B | Process Yield as % of theory | ¹H—NMR: δ (ppm) in CF₃CO₂D |
|---|---|---|---|---|
| 21 | —C(COOH)(CH₂—CH₂) (cyclopropyl) | cyclopenta-fused pyridinium | a(16) | 1.55–2.85(m, 6H, 4 cyclopropyl-H and 2 cyclopentene-H); 3.05–4.0(m, 6H, 4 cyclopentene-H and SCH₂); 5.15–6.25(m, 4H, CH₂Py and 2 lactam-H); 7.42(s, 1H, thiazole); 7.75–8.95(m, 3H, Py) |
| 22 | —C(COOH)(cyclobutyl) | cyclopenta-fused pyridinium | a(22) | 1.9–3.1(m, 8H, 2 cyclopentene-H 6 cyclobutyl-H); 3.1–3.9(m, 6H, 4 cyclopentene-H and SCH₂); 5,45(d, J=5Hz, lactam-H); 5.48 and 5.96(AB, J=14Hz, 2H, CH₂Py); 6.15(d, J=5Hz, lactam-H); 7.42(s, 1H, thiazole); 7.63–8.72(m, 3H, Py) |
| 23 | —C(COOH)(cyclopentyl) | cyclopenta-fused pyridinium | a(25) | 1.4–2.8(m, 10H, 2 cyclopentene-H and 8 cyclopentene-H); 3.1–3.9(m, 6H, 4-cyclopentene-H and SCH₂); 4.95–6.25(m, 4H, CH₂Py and 2 lactam-H); 7.42(s, 1H, thiazole); 7.63–8.82(m, 3H, Py) |
| 24 | —CH₂—C₆H₄—COOH | cyclopenta-fused pyridinium | a(32) | 2.17–2.86(m, 2H, cyclopentene-H); 2.92–3.98(m, 6H, 4-cyclopentene-H and SCH₂); 4.98–6.23(m, 6H, OCH₂—s to 5.46, CH₂Py and 2 lactam-H); 7.43(s, 1H, thiazole); 7.63–8.75(m, 7H, 4 phenyl-H, 3 Py—H) |

TABLE 4

[Structure: aminothiazole-oxime-amide-β-lactam with CH₂⁺—N pyridinium bearing a Substituent]

| Example | (CH₂)ₙ(A)ₘR² | Substituent | Process Yield as % of theory | ¹H—NMR: δ (ppm) in CF₃CO₂D |
|---|---|---|---|---|
| 25 | —CH₂CO₂K | 4-CH₃ | a (28) | 2,77 (s, 3H, CH₃); 3,42 and 3,82 (AB, J=19Hz, 2H, SCH₂); 4.9–6.35 (m, 6H, OCH₂ to 5.08, CH₂Py and 2 lactam-H); 7,42 (s, 1H, thiazole); 7.92 and 8.82 (AA'BB', J=6Hz, 4H, Py) |
| 26 | —CH₂CO₂K | 4-CH₂CH₂CH₃ | a (24) | 1.08 (t, J=7Hz, 3H, CH₃); 1.5–2.15 (m, 2H, CH₂); 1.65–3.17 (m, 2H, CH₂); 3.42 and 3.82 (AB, J=19Hz, 2H, SCH₂); 1.85–6.35 (m, 6H, OCH₂ to 5.08, CH₂Py and 2 lactam-H); 7.42 (s, 1H, thiazole); 7.93 and 8.83 (AA' BB', J=6Hz; 4H, Py) |
| 27 | —CH₂CO₂K | 3-CH₂OH | a (27) | 3.48 and 3.87 (AB, J=19Hz, 2H, SCH₂); 5.08 (s, 2H, NOCH₂); 5.20 (s, 2H, CH₂OH); 5.2–6,5 (m, 4H, CH₂Py and 2 lactam-H); 7.43 (s, 1H, thiazole); 7.6–9.25 (m, 4H, Py) |
| 28 | —CH₂CO₂K | 4-CH(OH)—CH₃ | a (29) | 1.64 (d, J=7Hz, CH₃); 3.45 and 3.86 (AB, J=19Hz, 2H, SCH₂); 4.9–6.4 (m, 6H, OCH₂ 5.07, CH₂Py and 2 lactam-H); 7.41 (s, 1H, thiazole); 8.22 and 8.98 (AA' BB', J=7Hz, 4H, Py) |
| 29 | —CH₂CO₂K | 4-OCH₃ | a (31) | 3.43 and 3.82 (AB, J=19Hz, 2H, SCH₂); 4.22 |

TABLE 4-continued

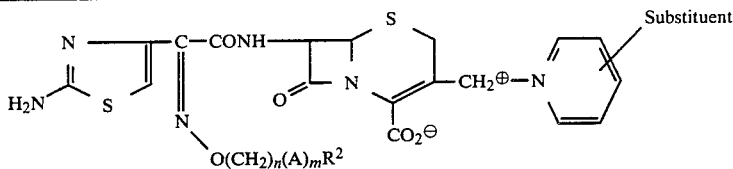

| Example | $(CH_2)_n(A)_mR^2$ | Substituent | Process Yield as % of theory | $^1H$—NMR: δ (ppm) in $CF_3CO_2D$ |
|---|---|---|---|---|
| | | | | (s, 3H, $OCH_3$); 5.08 (s, 2H, $OCH_2$); 5.2–6.25 (m, 4H, $CH_2Py$ and 2 lactam-H); 7.43 (s, 1H, thiazole); 7.48 and 8.75 (AA' BB', J=7Hz, 4H, Py) |
| 30 | —$CH_2CO_2K$ | 3-$C_6H_5$ | a (18) | 3.50 and 3.88 (AB, J=19Hz, 2H, $SCH_2$) 4.9–6.45 (m, 6H, $OCH_2$ to 5.07, $CH_2Py$ and 2 lactam-H); 7.42 (s, 1H, thiazole); 7.4–9.4 (m, 9H, 6 phenyl-H and 4 Py—H) |
| 31 | —$CH_2CO_2K$ | 3-Cl | a (22) | 3.50 and 3.89 (AB, J=19Hz, 2H, $SCH_2$); 5.08 (s, 2H, $OCH_2$); 5.1–6.45 (m, 4H, $CH_2Py$ and 2 lactam-H); 7.43 (s, 1H, thiazole); 7.6–9.25 (m, 4H, Py) |
| 32 | —$CH_2CO_2K$ | 4-$CH_2CH_2SO_3K$ | a (32) | 3.4–4.0 (m, 6H, $SCH_2$ and $CH_2CH_2$); 4.9–6.3 (m, 6H, $OCH_2$ to 5.09, $CH_2Py$ and 2 lactam-H); 7.42 (s, 1H, thiazole); 8.15 and 8.81 (AA' BB', J=7Hz, 4H, Py) |
| 33 | —$CH_2CO_2K$ | 3-$C_2H_5$ | a (28) | 1.58 (t, J=7Hz, 3H, $CH_2\underline{CH_3}$); 3.05 (q, J=7Hz, 2H, $\underline{CH_2}CH_3$); 3.43 and 3.83 (AB, J=19Hz, 2H, $SCH_2$); 4.85–6.33 (m, 6H, $OCH_2$ to 6.09, $CH_2Py$ and 2 lactam-H); 7.42 (s, 1H, thiazole); 7.85–9.05 (m, 4H, Py) |
| 34 | —$CH_2CO_2K$ | 3-$CH_3$—5-$CH_3$ | a (25) | 2.65 (s, 6H, $CH_3Py$); 3.45 and 3.79 (AB, J=19Hz, 2H, $SCH_2$); 4.8–6.3 (m, 6H, $OCH_2$ to 5.08, $CH_2Py$ and 2 lactam-H); 7.41 (s, 1H, thiazole); 8.15–8.61 (m, 3H, Py) |
| 35 | —$CH_2CO_2K$ | 4-$CH_2C_6H_5$ | a (15) | 3.43 and 3.84 (AB, J=19Hz, 2H, $SCH_2$); 4.35 (s, 2H, $\underline{CH_2}C_6H_5$); 4.9–6.35 (m, 6H, $OCH_2$ 5.07, $CH_2Py$ and 2 lactam-H); 7.03–7.51 (m, 6H, $C_6H_5$ and thiazole); 7.95 and 8.81 (AA' BB', J=6Hz, 4H, Py) |
| 36 | —$CH_2CO_2K$ | 3-OH | a (28) | 3.45 and 3.85 (AB, J=19Hz, 2H, $SCH_2$); 4.95–6.15 (m, 6H, $OCH_2$ to 5.07, $CH_2Py$ and 2 lactam-H); 7.41 (s, 1H, thiazole); 7.75–8.82 (m, 4H, Py) |
| 37 | —$CH_2CO_2K$ | 3-$CH_2CH_2CH_2OH$ | a (24) | 2.18 (m, 2H, propyl); 2.85–4.1 (m, 6H, $SCH_2$ and 4 propyl-H); 5.07 (s, 2H, $OCH_2$); 5.1–6.48 (m, 4H, $CH_2Py$ and 2 lactam-H); 7.42 (s, 1H, thiazole); 7.5–9.3 (m, 4H, Py) |
| 38 | —$CH_2CO_2K$ | 4-$CH_2OCH_3$ | a (28) | 3.46 and 3.80 (AB, J=19Hz, 2H, $SCH_2$); 3.72 (s, 3H, $CH_2OCH_3$, 4.92–6.41 (m, 8H, $\underline{CH_2}OCH_3$ to 4.97, $OCH_2$ to 5.08, $CH_2Py$ and 2 lactam-H); 7.39 (s, 1H, thiazole); 8.12 and 8.97 (AA'BB', J=6Hz, 4H, Py) |
| 39 | —$CH_2CO_2K$ | 3-$CH_2CH=CH_2$ | a (27) | 3.15–4.12 (m, 4H, CH—$\underline{CH_2}$ and $SCH_2$); 4.92–6.35 (m, 9H, $OCH_2$ to 5.08, $CH_2Py$, 2 lactam-H) and $\underline{CH}=CH_2$) 7.41 (s, 1H, thiazole); 7.85–8.91 (m, 4H, Py) |
| 40 | —$CH_2CO_2K$ | 3-$COC_6H_5$ | a (14) | 3.43 and 3.83 (AB, J=19Hz, 2H, $SCH_2$); 4.94–6.21 (m, 6H, $OCH_2$ to 5.08, $CH_2Py$ and 2 lactam-H); 7.35–9.41 (m, 10H, thiazole, $C_6H_5$ and Py) |
| 41 | —$CH_2CO_2K$ | 4-$CH_2COCH_3$ | a (22) | 2.55 (s, 3H, $CH_3$); 3.45 and 3.83 (AB, J=19Hz, 2H, $SCH_2$); 4.1–4.45 (m, 2H, $CH_2$); 4.95–6.35 (m, 6H, $OCH_2$ to 5.08, $CH_2Py$ and 2 lactam-H); 7.41 (s, 1H, thiazole); 8.11 and 8.96 (AA' BB', J=6Hz, 4H, Py) |
| 42 | —$CH_2CO_2K$ | 3-C(O-CH2-CH2-O)CH3 (dioxolane) | a (24) | 1.84 (s, 3H, $CH_3$); 3.46 and 3.88 (AB, J=19Hz, 2H, $SCH_2$); 3.92–4.55 (m, 4H, dioxolan-H); 4.9–6.35 (m, 6H, $OCH_2$ to 5.07, $CH_2Py$ and 2 lactam-H); 7.43 (s, 1H, thiazole); 7.95–9.36 (m, 3H, Py) |

TABLE 4-continued

| Example | $(CH_2)_n(A)_mR^2$ | Substituent | Process Yield as % of theory | $^1H$—NMR: δ (ppm) in $CF_3CO_2D$ |
|---|---|---|---|---|
| 43 | —$CH_2CO_2K$ | 3-cyclopentyl | a (18) | 1.35–4.05 (m, 11H, cyclopentyl and $SCH_2$); 4.95–6.31 (m, 6H, $OCH_2$ to 5.08, $CH_2Py$ and 2 lactam-H); 7.40 (s, 1H, thiazole); 7.85–8.86 (m, 4H, Py) |
| 44 | —$CH_2CO_2K$ | 3-cyclopentenyl | a (21) | 2.05–3.08 (m, 6H, cyclopentyl); 3.43 and 3.83 (AB, J=19Hz, 2H, $SCH_2$); 4.9–6.25 (m, 6H, $OCH_2$ to 5.08, $CH_2Py$ and 2 lactam-H); 6.81 (bs, 1H, cyclopentyl); 7.42 (s, 1H, thiazole); 7.85–8.91 (m, 4H, Py) |
| 45 | —$CH_2CO_2K$ | 3-(1-hydroxycyclopentyl) | a (18) | 2.01–2.4 (bs, 8H, cyclopentyl); 3.45 and 3.85 (AB, J=19Hz, 2H, $SCH_2$); 4.9–6.15 (m, 6H, $OCH_2$ to 5.07, $CH_2Py$ and 2 lactam-H); 7.39 (s, 1H, thiazole); 7.98–9.35 (m, 4H, Py) |
| 46 | —$CH_2CO_2K$ | 4-cyclohexyl | a (25) | 1.26–2.31 (m, 10H, $CH_2$—cyclohexyl); 2.8–4.05 (m, 3H, CH—cyclohexyl, $SCH_2$); 4.95–6.25 (m, 6H, $OCH_2$ to 5.09, $CH_2Py$ and 2 lactam-H); 7.40 (s, 1H, thiazole); 7.96 and 8.84 (AA′ BB′, J=6Hz, 4H, Py) |
| 47 | —$CH_2CO_2K$ | 4-tetrahydropyranyl | a (28) | 1.75–2.35 (m, 4H, pyranyl); 3.11–4.12 (m, 7H (5 pyranyl-H and $SCH_2$); 4.9–6.28 (m, 6H, $OCH_2$ to 5.08, $CH_2Py$ and 2 lactam-H); 7.40 (s, 1H, thiazole); 8.05 and 8.95 (AA′ BB′, J=6Hz, 4H, Py) |
| 48 | —$CH_2CO_2K$ | 2-$SCH_3$ | a (18) | 2.95 (s, 3H, $SCH_3$); 3.41 and 3.81 (AB, J=19Hz, 2H, $SCH_2$); 4.9–6.35 (m, 6H, $OCH_2$ to 5.08, $CH_2Py$ and 2 lactam-H); 7.38 (s, 1H, thiazole); 7.52–8.75 (m 4H, Py) |
| 49 | —$CH_2CO_2K$ | 4-$CH_2SCH_3$ | a (14) | 2.18 (s, 3H, $CH_3$); 3.42 and 3.82 (AB, J=19Hz, 2H, $SCH_2$); 3.95 (s, 2H, $CH_2S$); 4.9–6.22 (m, 6H, $OCH_2$ to 5.08, $CH_2Py$ and 2 lactam-H); 7.36 (s, 1H, thiazole); 8.12 and 8.92 (AA′ BB′, J=6Hz, 4H, Py) |
| 50 | —$CH_2CO_2K$ | 3-$CH_2SOCH_3$ | a (21) | 3.05 (s, 3H, $SOCH_3$); 3.55 and 3.82 (AB, J=19Hz, 2H, $SCH_2$); 4.55 (s, 2H, $CH_2SO$); 4.9–6.45 (m, 6H, $OCH_2$ to 5.05, $CH_2Py$ and 2 lactam-H); 7.36 (s, 1H, thiazole); 8.0–9.13 (m, 4H, Py) |
| 51 | —$CH_2CO_2K$ | 3-$CH_2SO_2CH_3$ | a (23) | 3.35 (s, 3H, $SO_2CH_3$); 3.51 and 3.85 (AB, J=19Hz, 2H, $SCH_2$); 4.85 (s, 2H, $CH_2SO_2$); 4.95–6,36 (m, 6H, $OCH_2$ to 5.06, $CH_2Py$ and 2 lactam-H); 7.38 (s, 1H, thiazole); 8.03–9.20 (m, 4H, Py) |
| 52 | —$CH_2CO_2K$ | 3-F | a (26) | 3.51 and 3.88 (AB, J=19Hz, 2H, $SCH_2$); 5.07 (s, 2H, $OCH_2$); 5.11–6.48 (m, 4H, $CH_2Py$ and 2 lactam-H) 7.41 (s, 1H, thiazole); 7.6–9.25 (m, 4H, Py) |
| 53 | —$CH_2CO_2K$ | 3-Br—4-$CH_3$ | a (18) | 2.83 (s, 3H, $CH_3$); 3.46 and 3.89 (AB, J=19Hz, 2H, $SCH_2$); 5.05 (s, 2H, $OCH_2$); 5.11–6.42 (m, 4H, $CH_2Py$ and 2 lactam-H); 7.41 (s, 1H, thiazole); 7.86 (d, J=6Hz, 1H, Py); 8.6–9.2 (m, 2H, Py) |
| 54 | —$CH_2CO_2K$ | 3-$CF_3$ | a (30) | 3.50 and 3.92 (AB, J=19Hz, 2H, $SCH_2$); 5.07 (s, 2H, $OCH_2$); 5.1–6.4 (m, 4H, $CH_2Py$ and 2 lactam-H); 7.40 (s, 1H, thiazole); 8.12–9.55 (m, 4H, Py) |
| 55 | —$CH_2CO_2K$ | 4-N=O pyridone | a (28) | 3.48 and 3.88 (AB, J=19Hz, 2H, $SCH_2$); 4.9–6.42 (m, 6H, $OCH_2$ to 5.09, $CH_2Py$ and 2 lactam-H); 7.42 (s, 1H, thiazole); 7.0–9.55 (m, 8H, Py) |
| 56 | —$CH_2CO_2K$ | 3-(2-Pyridyl) | a (31) | 3.55 and 3.96 (AB, J=19Hz, 2H, $SCH_2$); 5.05 (s, 2H, $OCH_2$); 5.23–6.58 (m, 4H, $CH_2Py$ and 2 lactam-H); 7.40 (s, 1H, thiazole); 8.1–9.9 (m, 8H, Py) |
| 57 | —$CH_2CO_2CH_3$ | 3-$CH_3$ | a (28) | 2.68 (s, 3H, $CH_3$); 3.43 and 3.84 (AB, J=19Hz, |

TABLE 4-continued

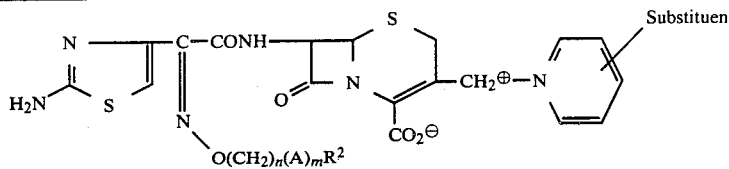

| Example | $(CH_2)_n(A)_mR^2$ | Substituent | Process Yield as % of theory | $^1$H—NMR: δ (ppm) in $CF_3CO_2D$ |
|---|---|---|---|---|
| | | | | 2H, $SCH_2$); 3.95 (s, 3H, $CO_2CH_3$); 4.85-6.45 (m, 6H, $OCH_2$ to 5.01, $CH_2Py$ and 2 lactam-H); 7.41 (s, 1H, thiazole); 7.83-9.0 (m, 4H, Py) |
| 58 | —$CH_2CO_2CH_3$ | 4-$OCH_3$ | a (27) | 3.43 and 3.80 (AB, J=19Hz, 2H, $SCH_2$); 3.95 (s, 3H, $CO_2CH_3$); 4.21 (s, 3H, $OCH_3$); 4.85-6.25 (m, 6H, $OCH_2$ to 5.02, $CH_2Py$ and 2 lactam-H); 7.41 (s, 1H, thiazole); 7.48 and 8.77 (AA′, BB′, J=7Hz, 4H, Py) |
| 59 | —$CH_2CO_2CH_3$ | 4-Cyclopropyl | b (58) | 1.1-2.6 (m, 5H, cyclopropyl); 3.42 and 3.82 (AB, J=19Hz, 2H, $SCH_2$); 3.95 (s, 3H, $CO_2CH_3$); 5.02 (s, 2H, $OCH_2$); 5.1-6.3 (m, 4H, $CH_2Py$ and 2 lactam-H); 7.41 (s, 1H, thiazole); 7.66 and 8.70 (AA′ BB′, J=7Hz, 4H, Py) |
| 60 | —$CH_2CO_2C_2H_5$ | 4-Cyclopropyl | a (31) | 1.01-1.95 (m, 7H, 4 cyclopropyl-H and $CH_2\underline{CH_3}$); 2.0-2.48 (m, 1H, cyclopropyl); 3.42 and 3.79 (AB, J=19Hz, 2H, $SCH_2$); 4.41 (q, J=7Hz, 2H, $\underline{CH_2}CH_3$); 4.83-6.28 (m, 6H, $OCH_2$ to 5.01, $CH_2Py$ and 2 lactam-H); 7.40 (s, 1H, thiazole); 7.65 and 8.68 (AA′ BB′, J=7Hz, 4H, Py) |
| 61 | —$C(CH_3)_2CO_2K$ | 4-$CH_3$ | a (31) | 1.78 (s, 6H, 2 × $CH_3$); 2.75 (s, 3H, $CH_3$); 3.43 and 3.82 (AB, J=19Hz, 2H, $SCH_2$); 5.1-6.3 (m, 4H, $CH_2Py$ and 2 lactam-H); 7.33 (s, 1H, thiazole); 7.87 and 8.74 (AA′ BB′, J=7Hz, 4H, Py) |
| 62 | —$C(CH_3)_2CO_2K$ | 4-$C(CH_3)_3$ | a (29) | 1.51 (s, 9H, t-Bu); 1.78 (s, 6H, 2 × $CH_3$); 3.45 and 3.86 (AB, J=19Hz, 2H, $SCH_2$); 5.15-6.35 (m, 4H, $CH_2Py$ and 2 lactam-H); 7.38 (s, 1H, thiazole); 8.13 and 8.88 (AA′ BB′, J=7Hz, 4H, Py) |
| 63 | —$C(CH_3)_2CO_2K$ | 4-Cyclopropyl | a (32) | 1.15-2.45 (m, 11H, s, $C(CH_3)_2$ to 1.77 and 5 cyclopropyl-H); 3.43 and 3.81 (AB, J=19Hz, 2H, $SCH_2$); 5.1-6.25 (m, 4H, $CH_2Py$ and 2 lactam-H); 7.38 (s, 1H, thiazole); 7.65 and 8.68 (AA′ BB′, J=7Hz, 4H, Py) |
| 64 | —$C(CH_3)_2CO_2K$ | 4-$COCH_3$ | a (24) | 1.79 (s, 6H, 2 × $CH_3$); 2.90 (s, 3H, $COCH_3$); 3.53 and 3.92 (AB, J=19Hz, 2H, $SCH_2$); 5.25-6.5 (m, 4H, $CH_2Py$ and 2 lactam-H); 7.39 (s, thiazole); 8.59 and 9.31 (AA′ BB′, J=7Hz, 4H, Py) |
| 65 | —$C(CH_3)_2CO_2K$ | 3-$OC_2H_5$ | a (32) | 1.57 (t, J=7Hz, 3H, $CH_2\underline{CH_3}$); 1.79 (s, 6H, 2 × $CH_3$); 3.45 and 3.85 (AB, J=19Hz, 2H, $SCH_2$); 4.33 (q, J=7Hz, 2H, $\underline{CH_2}CH_3$); 5.15-6.38 (m, 4H, $CH_2Py$ and 2 lactam-H); 7.40 (s, 1H, thiazole); 7.7-8.75 (m, 4H, Py) |
| 66 | —$C(CH_3)_2CO_2K$ | 3-$OCH(CH_3)_2$ | a (31) | 1.48 (d, J=6Hz, 6H, —$OCH(\underline{CH_3})_2$); 1.78 s, 6H, 2 × $CH_3$); 3.44 and 3.85 (AB, J=19Hz, 2H, $SCH_2$); 4.85 (m, 1H, $O\underline{CH}(CH_3)_2$); 5.15-6.35 (m, 4H, $CH_2Py$ and 2 lactam-H); 7.40 (s, 1H, thiazole); 7.6-8.7 (m, 4H, Py) |
| 67 | —$OCH_2\underset{\underset{CH_2}{\|}}{C}$—$CO_2K$ | 4-Cyclopropyl | b (52) | 1.1-2.6 (m, 5H, cyclopropyl-H); 3.42 and 3.83 (AB, J=19Hz, 2H, $SCH_2$); 5.02-6.3 (m, 6H, N—O—$CH_2$ to 5.18, $CH_2Py$ and 2 lactam-H); 6.63-7.16 (m, 2H, $C=CH_2$); 7.38 (s, 1H, thiazole); 7.65 and 8.88 (AA′ BB′, J=7Hz, 4H, Py) |
| 68 | —$\underset{\underset{CH_3}{\|}}{OCH}$—$CO_2K$ | 4-Cyclopropyl | b (55) | 1.05-2.55 (m, 8H, 5 cyclopropyl-H and d of CH—$CH_3$ to 1.75 with J=7Hz); 3.42 and 3.82 (AB, J=19Hz, 2H, $SCH_2$); 4.95-6.3 (m, 5H, $\underline{CH}$—$CH_3$, $CH_2Py$ and 2 lactam-H); 7.41 (s, 1H, thiazole); 7.63 and 8.68 (AA′ BB′, J=7Hz, 4H, Py) |

TABLE 4-continued

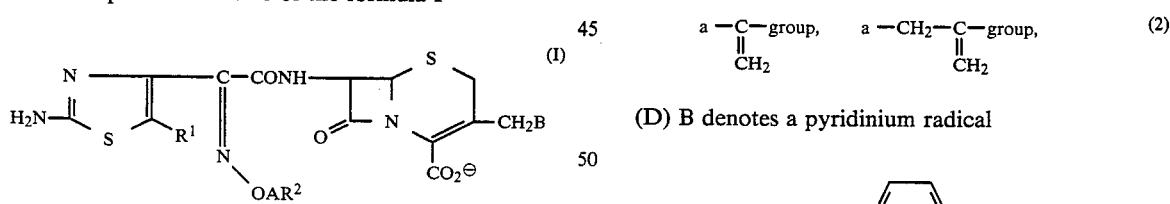

| Example | $(CH_2)_n(A)_mR^2$ | Substituent | Process Yield as % of theory | $^1H$—NMR: δ (ppm) in $CF_3CO_2D$ |
|---|---|---|---|---|
| 69 | —C—COOH (cyclopropyl) | 4-Cyclopropyl | b (38) | 1.1–2.8 (m, 11H, cyclobutyl and cyclopropyl-H); 3.40 and 3.80 (AB, J=19Hz, 2H, $SCH_2$); 5.43 (d, J= 5Hz, lactam-H); 5.45 and 5.94 (AB, J=14Hz, 2H, $CH_2Py$); 6.12 (d, J= 5Hz, lactam-H); 7.42 (s, 1H, thiazole); 7.65 and 8.71 (AA′ BB′, J=7Hz, 4H, Py) |
| 70 | —$CH_2CONH_2$ | 4-Cyclopropyl | a (24) | 1.0–2.5 (m, 5H, cyclopropyl-H); 3.43 and 3.79 (AB, J=19Hz, 2H, $SCH_2$); 5.06 (s, 2H, $OCH_2$); 5.15–6.30 (m, 4H, $CH_2Py$ and 2 lactam-H); 7.43 (s, 1H, thiazole); 7.63 and 8.73 (AA′, BB′, J= 4H, Py) |
| 71 | —$CH_2CONH_2$ | H | a (31)) | 3.55 and 3.83 (AB, J=19Hz, 2H, $SCH_2$); 5.06 (s, 2H, $OCH_2$); 5.16–6.25 (m, 4H, $CH_2Py$ and 2 lactam-H); 7.41 (s, 1H, thiazole); 7.7–9.2 (m, 5H, Py) |
| 72 | —$CH_2CONH_2$ | 3-$CH_2$ | a (28) | 2.68 (s, 3H, $CH_3$); 3.48 and 3.78 (AB, J=19Hz, 2H, $SCH_2$); 5.07 (s, 2H, $OCH_2$); 5.16–6.35 (m, 4H, $CH_2Py$ and 2 lactam-H); 7.43 (s, 1H, thiazole) 7.72–9.00 (m, 4H, Py) |
| 73 | —$CH_2CONH_2$ | 3-$CH_2OH$ | a (34) | 3.52 and 3.82 (AB, J=19Hz, 2H, $SCH_2$); 5.06 (s, 2H, $OCH_2$); 5.20 (s, 2H, $CH_2OH$); 5.1–6.4 (m, 4H, $CH_2Py$ and 2 lactam-H); 7.43 (s, 1H, thiazole); 7.72–9.25 (m, 4H, Py) |
| 74 | —$CH_2CONH_2$ | 3-Cl | a (25) | 3.55 and 3.88 (AB, J=19Hz, 2H, $SCH_2$); 5.08 (s, 2H, $OCH_2$); 5.2–6.4 (m, 4H, $CH_2Py$ and 2 lactam-H); 7.44 (s, 1H, thiazole); 7.7–9.25 (m, 4H, Py). |

We claim:

1. A cephem derivative of the formula I $$\text{(I)}$$

and its physiologically acceptable acids addition salts in which (A) $R^1$ denotes hydrogen, (B) $R^2$ denotes a group of —$CO_2R^3$ in which $R^3$ denotes hydrogen, $C_1$–$C_4$-alkyl, or one equivalent of an alkali metal, alkaline earth metal, or ammonium base, a nitrile group or a carbamoyl group —$CONH_2$ (C) A denotes (1) a group $$-\overset{R^4}{\underset{R^5}{C}}-$$

in which $R^4$ and $R^5$ can be identical or different and are individually hydrogen or a $C_1$–$C_4$-alkyl group or, $$a -\overset{\|}{\underset{CH_2}{C}}-\text{group}, \quad a -CH_2-\overset{\|}{\underset{CH_2}{C}}-\text{group}, \quad (2)$$

(D) B denotes a pyridinium radical $$-\oplus N$$

which can be monosubstituted or disubstituted by identical or different (1) $C_1$–$C_4$ alkyl groups,
 (a) wherein said ($C_1$–$C_4$ alkyl groups can be monosubstituted by hydroxyl; and
 (b) wherein two $C_1$–$C_4$ alkyl groups can also be linked to form a ring that contain 3 to 5 carbon atoms, (2) $C_3$–$C_6$-cycloalkyl, (3) $C_1$–$C_4$ alkoxy; and (4) halogen, and wherein the O—A—$R^2$ group in formula (I) is in the syn position, with the proviso that (i) $R^4$ and $R^5$ cannot both be hydrogen when $R^3$ is hydrogen or a $C_1$-$C_4$ alkyl, or (ii) $R^4$ and $R^5$ cannot be both a $C_1$-$C_4$ alkyl when $R^3$ is hydrogen.

2. A pharmaceutical formulation which is active against bacterial infections, containing an effective amount of cephem derivative of the formula I of claim 1 and one or more pharmacologically acceptable excipients or diluents.

3. A method of combatting bacterial infections comprising the step of administering to a host an effective amount of a cephem derivative of the formula I, as defined in claim 1 for combatting bacterial infections.

* * * * *